US012773215B2

(12) United States Patent
Bowman et al.

(10) Patent No.: US 12,773,215 B2
(45) **Date of Patent: *Oct. 27, 2026**

(54) IMPLANT DELIVERY DEVICE

(71) Applicant: MicroVention, Inc., Aliso Viejo, CA (US)

(72) Inventors: Heath Bowman, Aliso Viejo, CA (US); Jake Le, Aliso Viejo, CA (US); Matthew Fitz, Aliso Viejo, CA (US)

(73) Assignee: MICROVENTION, INC., Aliso Viejo, CA (US)

( * ) Notice: Subject to any disclaimer, the term of this patent is extended or adjusted under 35 U.S.C. 154(b) by 80 days.

This patent is subject to a terminal disclaimer.

(21) Appl. No.: 18/895,322

(22) Filed: Sep. 24, 2024

(65) Prior Publication Data

US 2025/0143715 A1 May 8, 2025

Related U.S. Application Data

(63) Continuation of application No. 17/663,368, filed on May 13, 2022, now Pat. No. 12,114,864, which is a (Continued)

(51) Int. Cl.
*A61B 17/12* (2006.01)
*A61F 2/95* (2013.01)
(Continued)

(52) U.S. Cl.
CPC .... *A61B 17/1214* (2013.01); *A61B 17/12027* (2013.01); *A61B 17/12099* (2013.01);
(Continued)

(58) Field of Classification Search
CPC .......... A61B 17/12022; A61B 17/1214; A61B 17/12099; A61B 17/12113;
(Continued)

(56) References Cited

U.S. PATENT DOCUMENTS 4,346,712 A 8/1982 Handa et al.
4,364,392 A 12/1982 Strother et al.
(Continued)

FOREIGN PATENT DOCUMENTS

EP 0547530 A1 6/1993
EP 0707830 A1 4/1996
(Continued)

OTHER PUBLICATIONS

Schmutz, F. et al. "Embolization of Cerebral Artriovenous Malformations with Silk: Histopathologic Changes and Hemorrhagic Complications", AJNR 18:7, Aug. 1997, pp. 1233-1237, 5 pages.
(Continued)

*Primary Examiner* — Diane D Yabut
(74) *Attorney, Agent, or Firm* — Procopio, Cory, Hargreaves & Savitch, LLP

(57) ABSTRACT

A system for delivering an implant within a patient is disclosed. The activation of the heater coil causes the degradation, melting or reduction of a component that brings the heater coil into or out of electrical contact with another component, or causes the individual loops of the coil to contact each other, thereby resulting a notable change in resistance in the circuit supplying the heater coil with electricity. A core wire terminates prior to the distal end of the device, allowing for greater flexibility.

19 Claims, 12 Drawing Sheets

Related U.S. Application Data continuation of application No. 16/698,561, filed on Nov. 27, 2019, now Pat. No. 11,357,513, which is a continuation of application No. 15/386,492, filed on Dec. 21, 2016, now Pat. No. 10,517,604, which is a continuation of application No. 13/081,275, filed on Apr. 6, 2011, now Pat. No. 9,561,125.

(60) Provisional application No. 61/324,246, filed on Apr. 14, 2010.

(51) Int. Cl.
*A61M 25/00* (2006.01)
*A61B 17/00* (2006.01)
*A61B 17/42* (2006.01)
*A61B 90/00* (2016.01)

(52) U.S. Cl.
CPC .. *A61B 17/12113* (2013.01); *A61B 17/12122* (2013.01); *A61B 17/12154* (2013.01); *A61F 2/95* (2013.01); *A61M 25/0021* (2013.01); *A61B 2017/00119* (2013.01); *A61B 2017/00477* (2013.01); *A61B 2017/00734* (2013.01); *A61B 2017/00867* (2013.01); *A61B 2017/12054* (2013.01); *A61B 2017/12068* (2013.01); *A61B 2017/12072* (2013.01); *A61B 2017/12077* (2013.01); *A61B 2017/1209* (2013.01); *A61B 2017/4233* (2013.01); *A61B 2090/3966* (2016.02); *A61F 2002/9505* (2013.01); *A61M 2025/0042* (2013.01)

(58) Field of Classification Search
CPC ........ A61B 17/12122; A61B 17/12154; A61B 17/12109; A61B 17/12131; A61B 2017/1205; A61B 2017/12068; A61B 2017/12077; A61B 2017/12072; A61B 2017/12054; A61B 2017/1209; A61M 25/0054; A61M 25/0053; A61M 2025/0915; A61M 2025/09166
See application file for complete search history.

(56) References Cited

U.S. PATENT DOCUMENTS 4,402,319 A 9/1983 Handa et al.
4,512,338 A 4/1985 Balko et al.
4,545,367 A 10/1985 Tucci
4,551,132 A 11/1985 Pasztor et al.
4,638,803 A 1/1987 Rand
RE32,348 E 2/1987 Pevsner
4,735,201 A 4/1988 O'Reilly
4,795,741 A 1/1989 Leshchiner et al.
4,819,637 A 4/1989 Dormandy, Jr. et al.
4,944,746 A 7/1990 Iwata et al.
4,994,069 A 2/1991 Ritchard et al.
5,108,407 A 4/1992 Geremia et al.
5,122,136 A 6/1992 Guglielmi et al.
5,133,731 A 7/1992 Butler et al.
5,147,317 A 9/1992 Shank et al.
5,147,370 A 9/1992 McNamara et al.
5,163,952 A 11/1992 Froix
5,217,484 A 6/1993 Marks
5,226,911 A 7/1993 Chee et al.
5,242,452 A 9/1993 Inoue
5,250,071 A 10/1993 Palermo
5,256,146 A 10/1993 Ensminger et al.
5,258,042 A 11/1993 Mehta
5,261,916 A 11/1993 Engelson
5,304,194 A 4/1994 Chee et al.
5,312,415 A 5/1994 Palermo et al.
5,333,620 A * 8/1994 Moutafis ............... A61M 25/09 600/585
5,334,201 A 8/1994 Cowan
5,334,210 A 8/1994 Gianturco
5,350,397 A 9/1994 Palermo et al.
5,354,295 A 10/1994 Guglielmi et al.
5,382,259 A 1/1995 Phelps et al.
5,382,260 A 1/1995 Dormandy, Jr. et al.
5,423,777 A 6/1995 Tajiri et al.
5,423,829 A 6/1995 Pham et al.
5,423,849 A 6/1995 Engleson et al.
5,443,454 A 8/1995 Tanabe et al.
5,443,478 A 8/1995 Purdy
5,443,495 A 8/1995 Buscemi et al.
5,469,867 A 11/1995 Schmitt
5,476,472 A 12/1995 Dormandy, Jr. et al.
5,498,227 A 3/1996 Mawad
5,522,836 A 6/1996 Palermo
5,525,334 A 6/1996 Ito et al.
5,529,653 A 6/1996 Glastra
5,536,274 A 7/1996 Neuss
5,569,245 A 10/1996 Guglielmi et al.
5,578,074 A 11/1996 Mirigian
5,580,568 A 12/1996 Greff et al.
5,582,619 A 12/1996 Ken
5,601,600 A 2/1997 Ton
5,612,050 A 3/1997 Rowe et al.
5,614,204 A 3/1997 Cochrum
5,624,449 A 4/1997 Pham et al.
5,624,461 A 4/1997 Mariant
5,624,685 A 4/1997 Takahashi et al.
5,634,936 A 6/1997 Linden et al.
5,639,277 A 6/1997 Mariant et al.
5,645,558 A 7/1997 Horton
5,658,308 A 8/1997 Snyder
5,667,767 A 9/1997 Greff et al.
5,669,931 A 9/1997 Kupiecki et al.
5,676,671 A 10/1997 Inoue
5,690,667 A 11/1997 Gia
5,690,671 A 11/1997 McGurk et al.
5,700,258 A 12/1997 Mirigian et al.
5,702,361 A 12/1997 Evans et al.
5,708,755 A 1/1998 Gronet et al.
5,718,711 A 2/1998 Berenstein et al.
5,722,989 A 3/1998 Fitch et al.
5,725,568 A 3/1998 Hastings
5,733,329 A 3/1998 Wallace et al.
5,743,905 A 4/1998 Eder
5,749,891 A 5/1998 Ken et al.
5,749,894 A 5/1998 Engelson
5,759,161 A 6/1998 Ogawa et al.
5,766,204 A 6/1998 Porter et al.
5,766,219 A 6/1998 Horton
5,792,154 A 8/1998 Doan et al.
5,800,454 A 9/1998 Jacobson et al.
5,800,455 A 9/1998 Palermo et al.
5,814,062 A 9/1998 Sepetka et al.
5,823,198 A 10/1998 Jones et al.
5,830,178 A 11/1998 Jones et al.
5,836,893 A * 11/1998 Urick .................... A61M 25/09 600/585
5,846,210 A 12/1998 Ogawa et al.
5,846,247 A 12/1998 Unsworth et al.
5,851,206 A 12/1998 Guglielmi et al.
5,851,508 A 12/1998 Greff et al.
5,891,058 A 4/1999 Taki et al.
5,895,385 A 4/1999 Guglielmi et al.
5,902,254 A 5/1999 Magram
5,911,737 A 6/1999 Lee et al.
5,925,059 A 7/1999 Palermo
5,941,888 A 8/1999 Engleson
5,944,733 A 8/1999 Guglielmi et al.
5,947,963 A 9/1999 Guglielmi et al.
5,964,771 A 10/1999 Beyar et al.
5,964,797 A 10/1999 Ho
5,976,131 A 11/1999 Guglielmi et al.
5,984,629 A 11/1999 Brodersen et al.
5,984,929 A 11/1999 Bashiri et al.
6,013,084 A 1/2000 Ken et al.
6,015,424 A 1/2000 Rosenbluth et al.
6,033,423 A 3/2000 Ken et al.

(56) References Cited

U.S. PATENT DOCUMENTS

| | | | |
|---|---|---|---|
| 6,059,815 A | 5/2000 | Lee et al. | |
| 6,086,599 A | 7/2000 | Lee et al. | |
| 6,159,206 A | 12/2000 | Ogawa | |
| 6,165,178 A | 12/2000 | Bashiri et al. | |
| 6,183,504 B1 | 2/2001 | Inoue | |
| 6,221,066 B1 | 4/2001 | Ferrera et al. | |
| 6,238,403 B1 | 5/2001 | Greene, Jr. et al. | |
| 6,277,126 B1 | 8/2001 | Barrey et al. | |
| 6,293,960 B1 | 9/2001 | Ken | |
| 6,296,622 B1 | 10/2001 | Kurz et al. | |
| 6,299,619 B1 | 10/2001 | Greene, Jr. et al. | |
| 6,371,979 B1 | 4/2002 | Beyar et al. | |
| 6,375,668 B1 | 4/2002 | Gifford et al. | |
| 6,375,669 B1 | 4/2002 | Rosenbluth et al. | |
| 6,383,204 B1 | 5/2002 | Ferrera et al. | |
| 6,425,893 B1 | 7/2002 | Guglielmi | |
| 6,454,780 B1 | 9/2002 | Wallace | |
| 6,478,773 B1 | 11/2002 | Gandhi et al. | |
| 6,500,149 B2 | 12/2002 | Gandhi et al. | |
| 6,526,979 B1 | 3/2003 | Nikolchev et al. | |
| 6,602,261 B2 | 8/2003 | Greene, Jr. et al. | |
| 6,602,269 B2 | 8/2003 | Wallace et al. | |
| 6,610,046 B1 | 8/2003 | Usami et al. | |
| 6,634,361 B1 | 10/2003 | Nikolchev et al. | |
| 6,656,173 B1 | 12/2003 | Palermo | |
| 6,684,884 B2 | 2/2004 | Nikolchev et al. | |
| 6,705,323 B1 | 3/2004 | Nikolchev et al. | |
| 6,740,073 B1 | 5/2004 | Saville | |
| 6,743,236 B2 | 6/2004 | Barry et al. | |
| 6,807,446 B2 | 10/2004 | Fenn et al. | |
| 6,849,081 B2 | 2/2005 | Sepetka et al. | |
| 6,855,125 B2 | 2/2005 | Shanley | |
| 6,966,892 B2 | 11/2005 | Gandhi et al. | |
| 7,001,422 B2 | 2/2006 | Escamilla et al. | |
| 7,014,645 B2 | 3/2006 | Greene et al. | |
| 7,048,719 B1 | 5/2006 | Monetti | |
| 7,166,122 B2 | 1/2007 | Aganon et al. | |
| 7,198,613 B2 | 4/2007 | Gandhi et al. | |
| 7,344,558 B2 | 3/2008 | Lorenzo et al. | |
| 7,367,987 B2 | 5/2008 | Balgobin et al. | |
| 7,371,251 B2 | 5/2008 | Mitelburg et al. | |
| 7,628,797 B2 | 12/2009 | Tieu et al. | |
| 7,651,513 B2 | 1/2010 | Teoh et al. | |
| 7,691,121 B2 | 4/2010 | Rosenbluth et al. | |
| 7,708,754 B2 | 5/2010 | Balgobin et al. | |
| 7,708,755 B2 | 5/2010 | Davis, III et al. | |
| 7,811,305 B2 | 10/2010 | Balgobin et al. | |
| 8,182,506 B2 | 5/2012 | Fitz et al. | |
| 8,192,480 B2 | 6/2012 | Tieu et al. | |
| 8,460,332 B2 | 6/2013 | Tieu et al. | |
| 9,242,070 B2 | 1/2016 | Tieu | |
| 2001/0044633 A1 | 11/2001 | Klint | |
| 2002/0107534 A1 | 8/2002 | Schaefer et al. | |
| 2002/0123755 A1 | 9/2002 | Lowe et al. | |
| 2002/0165537 A1* | 11/2002 | Kelley | A61M 25/09 606/41 |
| 2002/0173837 A1 | 11/2002 | Lauterjung | |
| 2002/0188341 A1 | 12/2002 | Elliott | |
| 2003/0014073 A1 | 1/2003 | Bashiri et al. | |
| 2003/0023262 A1 | 1/2003 | Welch | |
| 2003/0045901 A1 | 3/2003 | Opolski | |
| 2004/0034363 A1 | 2/2004 | Wilson et al. | |
| 2005/0043755 A1 | 2/2005 | Wilson et al. | |
| 2005/0113863 A1 | 5/2005 | Ramzipoor et al. | |
| 2005/0149108 A1 | 7/2005 | Cox | |
| 2005/0171572 A1 | 8/2005 | Martinez | |
| 2006/0025803 A1 | 2/2006 | Mitelberg et al. | |
| 2006/0052815 A1 | 3/2006 | Fitz et al. | |
| 2006/0166708 A1 | 7/2006 | Kim et al. | |
| 2006/0173488 A1 | 8/2006 | Takeuchi et al. | |
| 2006/0241682 A1 | 10/2006 | Kurz | |
| 2006/0241684 A1 | 10/2006 | Wilson et al. | |
| 2006/0241685 A1 | 10/2006 | Wilson et al. | |
| 2006/0253149 A1 | 11/2006 | Ghandi et al. | |
| 2006/0271097 A1 | 11/2006 | Ramzipoor et al. | |
| 2006/0271098 A1 | 11/2006 | Peacock, III | |
| 2006/0276826 A1 | 12/2006 | Mitelberg et al. | |
| 2006/0276829 A1 | 12/2006 | Balgobin et al. | |
| 2007/0055302 A1 | 3/2007 | Henry et al. | |
| 2007/0239196 A1 | 10/2007 | Pomeranz | |
| 2007/0270903 A1 | 11/2007 | Davis, III et al. | |
| 2008/0045997 A1 | 2/2008 | Balgobin et al. | |
| 2008/0119891 A1 | 5/2008 | Miles et al. | |
| 2008/0133028 A1 | 6/2008 | Wilson et al. | |
| 2008/0140111 A1 | 6/2008 | Wilson et al. | |
| 2008/0147201 A1 | 6/2008 | Wilson et al. | |
| 2008/0283066 A1 | 11/2008 | Delgado et al. | |
| 2009/0054905 A1 | 2/2009 | Levy | |
| 2009/0062812 A1 | 3/2009 | Fitz et al. | |
| 2009/0163780 A1 | 6/2009 | Tieu | |
| 2010/0094395 A1 | 4/2010 | Kellett | |
| 2010/0106162 A1 | 4/2010 | Jaeger et al. | |
| 2010/0160944 A1* | 6/2010 | Teoh | A61B 17/12154 606/191 |
| 2010/0268201 A1 | 10/2010 | Tieu et al. | |
| 2010/0268204 A1 | 10/2010 | Tieu | |
| 2011/0046282 A1 | 2/2011 | Mizuta et al. | |
| 2011/0118776 A1* | 5/2011 | Chen | A61B 17/12022 606/200 |
| 2013/0245745 A1 | 9/2013 | Vong et al. | |

FOREIGN PATENT DOCUMENTS

| | | |
|---|---|---|
| EP | 0719522 A1 | 7/1996 |
| EP | 0826342 A1 | 3/1998 |
| EP | 0948935 A1 | 10/1999 |
| EP | 0992220 A1 | 4/2000 |
| EP | 1073377 B1 | 2/2001 |
| EP | 0824010 B1 | 2/2003 |
| EP | 0830873 B1 | 4/2004 |
| EP | 1985240 A1 | 10/2008 |
| JP | 56-43962 A | 4/1981 |
| JP | 01-238874 A | 9/1989 |
| JP | H07-205918 A | 3/1995 |
| JP | 07-265431 A | 10/1995 |
| JP | 08-506033 A | 7/1996 |
| JP | 10-94542 A | 4/1998 |
| WO | 1991013592 A1 | 9/1991 |
| WO | 1993013712 A1 | 7/1993 |
| WO | 1994006503 A1 | 5/1994 |
| WO | 1994010936 A1 | 5/1994 |
| WO | 1995007667 A1 | 3/1995 |
| WO | 1995027443 A1 | 10/1995 |
| WO | 1996000034 A1 | 1/1996 |
| WO | 1996000104 A1 | 1/1996 |
| WO | 1997026939 A1 | 7/1997 |
| WO | 1997027888 A1 | 8/1997 |
| WO | 1998029042 A1 | 7/1998 |
| WO | 1998037816 A1 | 9/1998 |
| WO | 1998040033 A3 | 9/1998 |
| WO | 1999002094 A1 | 1/1999 |
| WO | 1999009894 A1 | 3/1999 |
| WO | 1999029260 A2 | 6/1999 |
| WO | 1999040852 A1 | 8/1999 |
| WO | 1999042059 A2 | 8/1999 |
| WO | 1999055239 A1 | 11/1999 |
| WO | 2000012031 A1 | 3/2000 |
| WO | 2000053105 A1 | 9/2000 |
| WO | 2000072781 A2 | 12/2000 |
| WO | 2001058366 A1 | 8/2001 |
| WO | 2002055146 A1 | 7/2002 |

OTHER PUBLICATIONS

Graves, V.B. et al., "Endovascular Occlusion of the Carotid or Vertebral Artery with Temporary Proximal flow Arrest and Microcoils: Clinical Results", AJNR 18:7, Aug. 1997, pp. 1201-1206, 6 pages.
Vinuela, F. M.D. et al. "Guglielmi detachable coil embolization of acute intracranial aneurysm: perioperative anatomical and clinical

(56) References Cited

OTHER PUBLICATIONS outcome in 403 patients" j Neurosurg 86:475-482, Mar. 1997, 8 pages.

* cited by examiner

Direct Current (DC)
Signaling

Alternating Current (AC)
Signaling

IMPLANT DELIVERY DEVICE

RELATED APPLICATIONS

This application is a continuation of and claims priority to U.S. patent application Ser. No. 17/663,368 filed May 13, 2022 entitled Implant Delivery Device, which is a continuation of U.S. patent application Ser. No. 16/698,561 filed Nov. 27, 2019 entitled Implant Delivery Device, which is a continuation of and claims priority to U.S. patent application Ser. No. 15/386,492 filed Dec. 21, 2016 entitled Implant Delivery Device (now U.S. Pat. No. 10,517,604 issued Dec. 31, 2019), which is a continuation of and claims priority to U.S. patent application Ser. No. 13/081,275 filed Apr. 6, 2011 entitled Implant Delivery Device (now U.S. Pat. No. 9,561,125 issued Feb. 7, 2017), which claims benefit of and priority to U.S. Provisional Application Ser. No. 61/324,246 filed Apr. 14, 2010 entitled Implant Delivery Device, all of which are hereby incorporated by reference in their entireties.

FIELD OF THE INVENTION

The present invention relates to systems and methods for delivering implant devices to a target site or location within the body of a patient. The present invention also relates to a method of detecting implant detachment within the body of a patient.

BACKGROUND OF THE INVENTION

Delivery of implantable therapeutic devices by less invasive means has been demonstrated to be desirable in numerous clinical situations. For example, vascular embolization has been used to control vascular bleeding, to occlude the blood supply to tumors, to occlude fallopian tubes, and to occlude vascular aneurysms, particularly intracranial aneurysms. In recent years, vascular embolization for the treatment of aneurysms has received much attention. Implants used to treat aneurysms are often convoluted or coiled lengths of wound wire and are referred to as "microcoils." Microcoils work by filling an aneurysm causing the blood flow through the aneurysm to slow or stop, thereby inducing thrombosis within the aneurysm.

Microcoils are extremely flexible and have very little structural integrity. In order to make them easier to retrieve and reposition, recent efforts have been directed to making them stretch-resistant. For example, a stretch-resistant embolic coil having a stretch-resistant member passing through the interior lumen of the coil is described in U.S. Pat. No. 5,582,619 to Ken. US Patent Publication No. 2004/0034363 to Wilson also discloses an embolic coil with a stretch resistant member having a distal end attached near the distal end of the coil and a proximal end of the member attached to a delivery catheter.

Several different treatment modalities have been employed in the prior art for deploying implant devices. For example, numerous repositionable detachment systems for implant devices have been described in the prior art including U.S. Pat. No. 5,895,385 to Guglielmi et al. and U.S. Pat. No. 5,108,407 to Geremia et al., the contents of which are hereby incorporated by reference. Several systems, such as those disclosed in U.S. Pat. No. 6,500,149 to Gandhi et al. and U.S. Pat. No. 4,346,712 to Handa et al., the contents of which are hereby incorporated by reference, describe the use of a heater to detach and deploy the implant device.

While implant delivery and detachment systems are known in the art, they do not provide the user feedback that the implant has indeed detached from the delivery device. This is especially important in cases where the detachment relies on the application of heat or an electrolytic process where an element of time is involved. These delivery devices leave the user in the position of wondering whether heat etc., has been applied long enough to cause detachment. Hence, there exists a need for a method of detecting whether an implant has properly and effectively detached within the body of a patient.

SUMMARY OF THE INVENTION

The present invention is an implant delivery and detachment system used to position and deploy implantable devices such as coils, stents, filters, and the like within a body cavity including, but not limited to, blood vessels, fallopian tubes, malformations such as fistula and aneurysms, heart defects (e.g. left atrial appendages and sepal openings), and other luminal organs.

The system comprises an implant, a delivery catheter (generically referred to as the pusher or delivery pusher), a detachable joint for coupling the implant to the pusher, a heat generating apparatus (generically referred to as the heater), and a power source to apply energy to the heater.

The present invention also includes a method for detecting detachment of an implant. In particular, detachment of an implant is detected by measuring the change in the electrical resistance of the delivery system.

The present invention may also be used in conjunction with the delivery mechanism disclosed in U.S. patent application Ser. No. 11/212,830 filed Aug. 25, 2005 entitled "Thermal detachment system for implanting devices," which is incorporated by reference herein in its entirety.

In one aspect of the present invention, the implant is coupled to the pusher using a tether, string, thread, wire, filament, fiber, or the like. Generically this is referred to as the tether. The tether may be in the form of a monofilament, rod, ribbon, hollow tube, or the like. Many materials can be used to detachably join the implant to the pusher. One class of materials are polymers such as polyolefin, polyolefin elastomer such as those made by Dow marketed under the trade name Engage or Exxon marketed under the trade name Affinity, polyethylene, polyester (PET), polyamide (Nylon), polyurethane, polypropylene, block copolymer such as PEBAX or Hytrel, and ethylene vinyl alcohol (EVA); or rubbery materials such as silicone, latex, and Kraton. In some cases, the polymer may also be cross-linked with radiation to manipulate its tensile strength and melt temperature. Another class of materials is metals such as nickel titanium alloy (Nitinol), gold, and steel. The selection of the material depends on the capacity of the material to store potential energy, the melting or softening temperature, the power used for detachment, and the body treatment site. The tether may be joined to the implant and/or the pusher by welding, knot tying, soldering, adhesive bonding, or other means known in the art. In one embodiment where the implant is a coil, the tether may run through the inside lumen of the coil and be attached to the distal end of the coil. This design not only joins the implant to the pusher, but also imparts stretch resistance to the coil without the use of a secondary stretch resistant member. In other embodiments where the implant is a coil, stent, or filter; the tether is attached to the proximal end of the implant.

In another aspect of the present invention, the tether detachably coupling the implant to the pusher acts as a reservoir of stored (i.e. potential) energy that is released during detachment. This advantageously lowers the time and energy required to detach the implant because it allows the tether to be severed by application of heat without necessarily fully melting the material. The stored energy also may exert a force on the implant that pushes it away from the delivery catheter. This separation tends to make the system more reliable because it may prevent the tether from re-solidifying and holding the implant after detachment. Stored energy may be imparted in several ways. In one embodiment, a spring is disposed between the implant and pusher. The spring is compressed when the implant is attached to the pusher by joining one end of the tether to one of either the pusher or implant, pulling the free end of the tether until the spring is at least partially compressed, then affixing the free end of the tether to the other of the implant or the pusher. Since both ends of the tether are restrained, potential energy in the form of tension on the tether (or compression in the spring) is stored within the system. In another embodiment, one end of the tether is fixed as in the previous embodiment, and then the tether is placed in tension by pulling on the free end of the tether with a pre-determined force or displacement. When the free end of the tether is then affixed, the elongation (i.e. elastic deformation) of the tether material itself stores energy.

In another aspect of the present invention, a heater is disposed on or within the pusher, typically, but not necessarily, near the distal end of the pusher. The heater may be attached to the pusher by, for example, soldering, welding, adhesive bonding, mechanical boding, or other techniques known in the art. The heater may be in the form of a wound coil, heat pipe, hollow tube, band, hypotube, solid bar, toroid, or similar shape. The heater may be made from a variety of materials such as steel, chromium cobalt alloy, platinum, silver, gold, tantalum, tungsten, mangalin, chromium nickel alloy available from California Fine Wire Company under the trade name Stable Ohm, conductive polymer, or the like. The tether is disposed in proximity to the heater. The tether may pass through the lumen of a hollow or coil-type heater or may be wrapped around the heater. Although the tether may be disposed in direct contact with the heater, this is not necessary. For ease of assembly, the tether may be disposed be in proximity to, but not actually touching, the heater.

The delivery catheter or pusher is an elongate member with distal and proximal ends adapted to allow the implant to be maneuvered to the treatment site. The pusher comprises a core mandrel and one or more electrical leads to supply power to the heater. The pusher may taper in dimension and/or stiffness along the length, with the distal end usually being more flexible than the proximal end. In one embodiment, the pusher is adapted to be telescopically disposed within a delivery conduit such as a guide catheter or microcatheter. In another embodiment, the pusher contains an inner lumen allowing it to be maneuvered over a guide wire. In still another embodiment, the pusher can be maneuvered directly to the treatment site without a secondary device. The pusher may have a radiopaque marking system visible with fluoroscopy that allows it to be used in conjunction with radiopaque markings on the microcatheter or other adjunctive devices.

In another aspect of the present invention, the core mandrel is in the form of a solid or hollow shaft, wire, tube, hypotube, coil, ribbon, or combination thereof. The core mandrel may be made from plastic materials such as PEEK, acrylic, polyamide, polyimide, Teflon, acrylic, polyester, block copolymer such as PEBAX, or the like. The plastic member(s) may be selectively stiffened along the length with reinforcing fibers or wires made from metal, glass, carbon fiber, braid, coils, or the like. Alternatively, or in combination with plastic components, metallic materials such as stainless steel, tungsten, chromium cobalt alloy, silver, copper, gold, platinum, titanium, nickel titanium alloy (Nitinol), and the like may be used to form the core mandrel. Alternatively, or in combination with plastic and/or metallic components, ceramic components such as glass, optical fiber, zirconium, or the like may be used to form the core mandrel. The core mandrel may also be a composite of materials. In one embodiment, the core mandrel comprises an inner core of radiopaque material such as platinum or tantalum and an outer covering of kink-resistant material such as steel or chromium cobalt. By selectively varying the thickness of the inner core, radiopaque identifiers can be provided on the pusher without using secondary markers. In another embodiment, a core material, for example stainless steel, with desirable material properties such as kink resistance and/or compressive strength is selectively covered (by, for example, plating, drawing, or similar methods known in the art) with a low electrical resistance material such as copper, aluminum, gold, or silver to enhance its electrical conductivity, thus allowing the core mandrel to be used as an electrical conductor. In another embodiment, a core material, for example, glass or optical fiber, with desirable properties such as compatibility with Magnetic Resonance Imaging (MRI), is covered with a plastic material such as PEBAX or polyimide to prevent the glass from fracturing or kinking.

In another aspect of the present invention, the heater is attached to the pusher, and then one or more electrical conductors are attached to the heater. In one embodiment a pair of conductive wires run substantially the length of the pusher and are coupled to the heater near the distal end of the pusher and to electrical connectors near the proximal end of the pusher. In another embodiment, one conductive wire runs the substantially the length of the pusher and the core mandrel itself is made from a conductive material or coated with a conductive material to act as a second electrical lead. The wire and the mandrel are coupled to the heater near the distal end and to one or more connectors near the proximal end of the pusher. In another embodiment, a bipolar conductor is coupled to the heater and is used in conjunction with radiofrequency (RF) energy to power the heater. In any of the embodiments, the conductor(s) may run in parallel to the core mandrel or may pass through the inner lumen of a substantially hollow core mandrel (for example, a hypotube).

In another aspect of the present invention, an electrical and/or thermally insulating cover or sleeve may be placed over the heater. The sleeve may be made from insulating materials such as polyester (PET), Teflon, block copolymer, silicone, polyimide, polyamide, and the like.

In another aspect of the present invention, electrical connector(s) are disposed near the proximal end of the pusher so that the heater can be electrically connected to a power source through the conductors. In one embodiment, the connectors are in the form of a plug with one or more male or female pins. In another embodiment, the connector(s) are tubes, pins, or foil that can be connected with clip-type connectors. In another embodiment, the connector(s) are tubes, pins, or foil that are adapted to mate with an external power supply.

In another aspect of the present invention, the pusher connects to an external power source so that the heater is electrically coupled to the power source. The power source may be from battery(s) or connected to the electrical grid by a wall outlet. The power source supplies current in the form of direct current (DC), alternating current (AC), modulated direct current, or radiofrequency (RF) at either high or low frequency. The power source may be a control box that operates outside of the sterile field or may be a hand-held device adapted to operate within a sterile field. The power source may be disposable, rechargeable, or may be reusable with disposable or rechargeable battery(s).

In another aspect of the present invention, the power source may comprise an electronic circuit that assists the user with detachment. In one embodiment, the circuit detects detachment of the implant and provides a signal to the user when detachment has occurred. In another embodiment, the circuit comprises a timer that provides a signal to the user when a pre-set length of time has elapsed. In another embodiment, the circuit monitors the number of detachments and provides a signal or performs an operation such as locking the system off when a pre-set number of detachments have been performed. In another embodiment, the circuit comprises a feedback loop that monitors the number of attachment attempts and increases the current, voltage, and/or detachment time in order to increase the likelihood of a successful detachment.

In another aspect of the present invention, the construction of the system allows for extremely short detachment time. In one embodiment the detachment time is less than 1 second.

In another aspect of the present invention, the construction of the system minimizes the surface temperature of the device during detachment. In one embodiment, the surface temperature at the heater during detachment is under 50° C. In another embodiment, the surface temperature at the heater during detachment is under 42° C.

In another aspect of the present invention, detachment of the implant is detected by measuring a change in the electrical resistance of the delivery system, specifically the heater zone, to detect implant detachment.

These and other aspects and features of the present invention will be appreciated upon consideration of the following drawings and detailed descriptions.

DETAILED DESCRIPTION OF THE INVENTION

Figure 1:
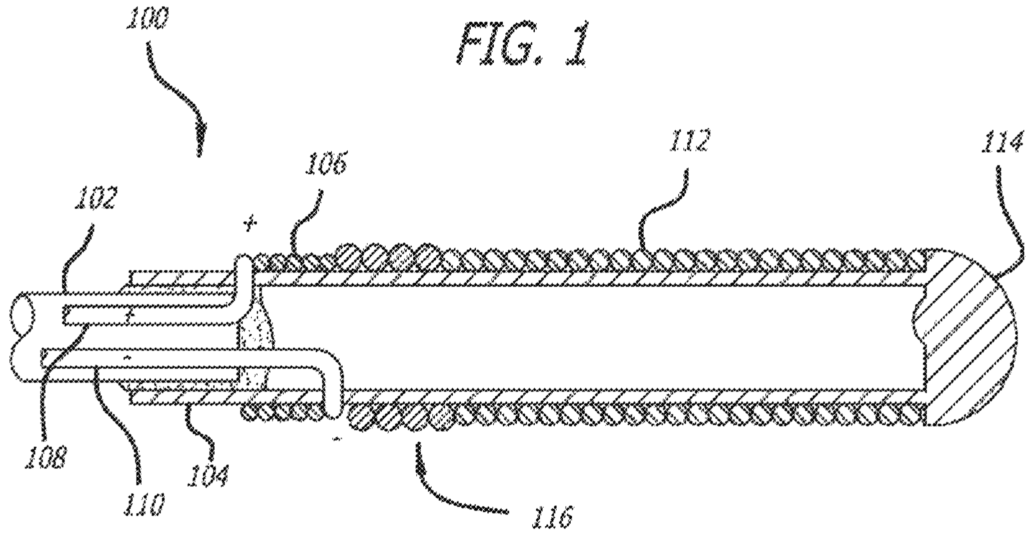
FIG. 1 illustrates a cross-sectional side view of a first embodiment of a detachment system according to the present invention.

Turning to FIG. 1, a detachment system 100 of the present invention, and specifically the distal portion of the detachment system 100, is illustrated. The detachment system 100 includes a pusher 102 that is preferably flexible. The pusher 102 is configured for use in advancing an implant device 112 into and within the body of a patient and, specifically, into a target cavity site for implantation and delivery of the implant device 112. Potential target cavity sites include but are not limited to blood vessels and vascular sites (e.g., aneurysms and fistula), heart openings and defects (e.g., the left atrial appendage), and other luminal organs (e.g., fallopian tubes).

A stretch-resistant tether 104 detachably couples the implant 112 to the pusher 102. In this example, the tether 104 is a plastic tube that is bonded to the pusher 102. A substantially solid cylinder could also be a design choice for the tether 104. The stretch resistant tether 104 extends at least partially through the interior lumen of an implant device 112.

Near the distal end of the pusher 102, a heater 106 is disposed in proximity to the stretch resistant tether 104. The heater 106 may be wrapped around the stretch resistant tether 104 such that the heater 106 is exposed to or otherwise in direct contact with the blood or the environment, or alternatively may be insulated by a sleeve, jacket, epoxy, adhesive, or the like. The pusher 102 comprises a pair of electrical wires, positive electrical wire 108 and negative electrical wire 110. The wires 108 and 110 are coupled to the heater 106 by any suitable means, such as, e.g., by welding or soldering.

The electrical wires 108, 110 are capable of being coupled to a source of electrical power (not shown). As illustrated the negative electrical wire 110 is coupled to the distal end of the heater 106 and the positive electrical wire 108 is coupled to the proximal end of the heater 106. In another embodiment, this configuration may be reversed, i.e., the negative electrical wire 110 is coupled to the proximal end of the heater 106 while the positive electrical wire 108 is coupled to the distal end of the heater 106.

Energy is applied to the heater 106 from the electrical wires 108, 110 in order to sever the portion of the tether 104 in the proximity of the heater 106. It is not necessary for the heater 106 to be in direct contact with the tether 104. The heater 106 merely should be in sufficient proximity to the tether 104 so that heat generated by the heater 106 causes the tether 104 to sever. As a result of activating the heater 106, the section of the stretch resistant tether 104 that is approximately distal from the heater 106 and within the lumen of an implant device 112 is released from the pusher 102 along with the implant device 112.

As illustrated, the implant device 112 is an embolic coil. An embolic coil suitable for use as the implant device 112 may comprise a suitable length of wire formed into a helical microcoil. The coil may be formed from a biocompatible material including platinum, rhodium, palladium, rhenium, tungsten, gold, silver, tantalum, and various alloys of these metals, as well as various surgical grade stainless steels. Specific materials include the platinum/tungsten alloy known as Platinum 479 (92% Pt, 8% W, available from Sigmund Cohn, of Mount Vernon, N.Y.) and nickel/titanium alloys (such as the nickel/titanium alloy known as Nitinol).

Another material that may be advantageous for forming the coil is a bimetallic wire comprising a highly elastic metal with a highly radiopaque metal. Such a bimetallic wire would also be resistant to permanent deformation. An example of such a bimetallic wire is a product comprising a Nitinol outer layer and an inner core of pure reference grade platinum, available from Sigmund Cohn, of Mount Vernon, N.Y., and Anomet Products, of Shrewsbury, Mass.

Commonly-assigned U.S. Pat. No. 6,605,101 provides a further description of embolic coils suitable for use as the implant device 112, including coils with primary and secondary configurations wherein the secondary configuration minimizes the degree of undesired compaction of the coil after deployment. The disclosure of U.S. Pat. No. 6,605,101 is fully incorporated herein by reference. Furthermore, the implant device 112 may optionally be coated or covered with a hydrogel or a bioactive coating known in the art.

The coil-type implant device 112 resists unwinding because the stretch resistant tether 104 that extends through the lumen of the implant device 112 requires substantially more force to plastically deform than the implant device 112 itself. The stretch resistant tether 104 therefore assists in preventing the implant device 112 from unwinding in situations in which the implant device 112 would otherwise unwind.

During assembly, potential energy may be stored within the device to facilitate detachment. In one embodiment, an optional spring 116 is placed between the heater 106 and the implant device 112. The spring is compressed during assembly and the distal end of the tether 104 may be tied or coupled to the distal end of the implant device 112, or may be melted or otherwise formed into an atraumatic distal end 114.

In one embodiment, the stretch resistant tether 104 is made from a material such as a polyolefin elastomer, polyethylene, or polypropylene. One end of the tether 104 is attached to the pusher 102 and the free end of the tether 104 is pulled through the implant 112 with the proximal end of the implant 112 flush to either the heater 106 (if no spring 116 is present) or to the compressed spring 116. A pre-set force or displacement is used to pre-tension the tether 104, thus storing energy in an axial orientation (i.e. co-linear or parallel to the long axis of the pusher 102) within the tether 104. The force or displacement depends on the tether material properties, the length of the tether 104 (which itself depends on the tether's attachment point on the pusher and the length of the implant). Generally, the force is below the elastic limit of the tether material, but sufficient to cause the tether to sever quickly when heat is applied. In one preferred embodiment wherein the implant to be deployed is a cerebral coil, the tether has a diameter within the range of approximately 0.001 to 0.007 inches. Of course the size of the tether can be changed to accommodate different types and sizes of other implants as necessary.

Figure 2:
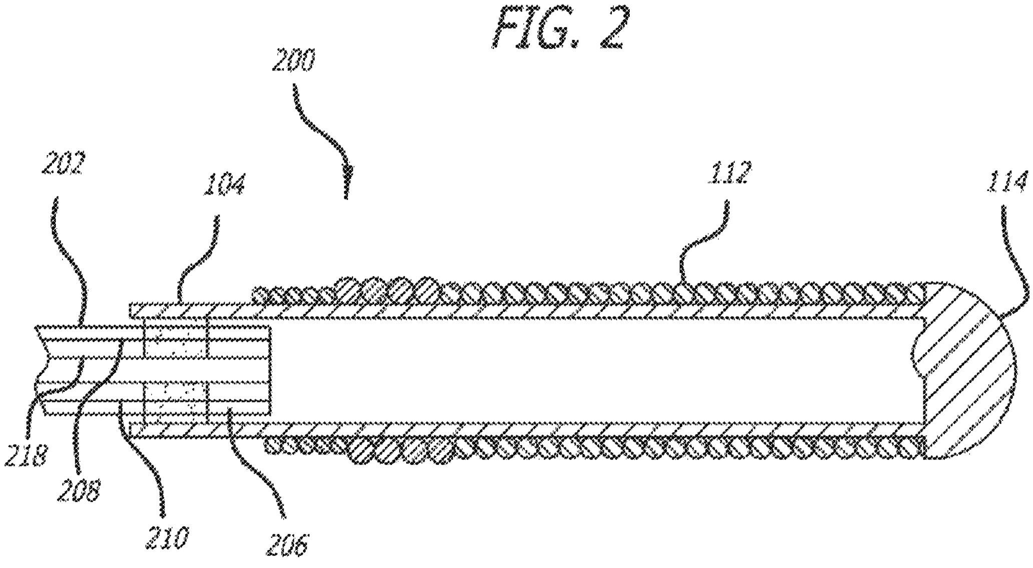
FIG. 2 illustrates a cross-sectional side view of a second embodiment of a detachment system according to the present invention.

Turning to FIG. 2, another embodiment of a detachment system of the present invention, detachment system 200, is illustrated. Detachment system 200 shares several common elements with detachment system 100. For example, the same devices usable as the implant device 112 with detachment system 100 are also usable as the implant device 112 with detachment system 200. These include, e.g., various embolic microcoils and coils. The implant device 112 has been previously described with respect to detachment system 100. As with the implant device 112, the same identification numbers are used to identify other elements/components of detachment system 100 that may correspond to elements/components of detachment system 200. Reference is made to the description of these elements in the description of detachment system 100 as that description also applies to these common elements in detachment system 200.

With detachment system 200, an interior heating element 206 is used to separate a section of a stretch resistant tube 104 and an associated implant device 112 from the detachment system 200. Detachment system 200 includes a delivery pusher 202 that incorporates a core mandrel 218. The detachment system 200 further includes a positive electrical wire 208 and a negative electrical wire 210 that extend through the lumen of the delivery pusher 202.

To form the internal heating element 206, the positive electrical wire 208 and the negative electrical wire 210 may be coupled to the core mandrel 218 of the delivery pusher 202. Preferably, the electrical wires 208, 210 are coupled to a distal portion of the core mandrel 218.

In one embodiment, the positive electrical wire 208 is coupled to a first distal location on the core wire 218, and the negative electrical wire 210 is coupled to a second distal location on the core wire 218, with the second distal location being proximal to the first distal location. In another embodiment, the configuration is reversed, i.e., the positive electrical wire 208 is coupled to the second distal location and the negative electrical wire 210 is coupled to the first distal location on the core wire 218. When the positive electrical wire 208 and the negative electrical wire 210 are coupled to the distal portion of the core mandrel 218, the distal portion of the core mandrel 218 along with the electrical wires 208, 210 forms a circuit that is the interior heating element 206.

The heater 206 increases in temperature when a current is applied from a power source (not shown) that is coupled to the positive electrical wire 208 and the negative electrical wire 210. If a greater increase in temperature/higher degree of heat is required or desired, a relatively high resistance material such as platinum or tungsten may be coupled to the distal end of the core mandrel 218 to increase the resistance of the core mandrel 218. As a result, higher temperature increases are produced when a current is applied to the heater 206 than would be produced with a lower resistance material. The additional relatively high resistance material coupled to the distal end of the core mandrel 218 may take any suitable form, such as, e.g., a solid wire, a coil, or any other shape or material as described above.

Because the heater 206 is located within the lumen of the tube-shaped tether 104, the heater 206 is insulated from the body of the patient. As a result, the possibility of inadvertent damage to the surrounding body tissue due to the heating of the heater 206 may be reduced.

When a current is applied to the heater 206 formed by the core mandrel 218, the positive electrical wire 208, and the negative electrical wire 210, the heater 206 increases in temperature. As a result, the portion of the stretch resistant tether 104 in proximity to the heater 206 severs and is detached, along with the implant device 112 that is coupled to the tether 104, from the detachment system 200.

In one embodiment of the detachment system 200, the proximal end of the stretch resistant tether 104 (or the distal end of a larger tube (not shown) coupled to the proximal end of the stretch resistant tether 104) may be flared in order to address size constraints and facilitate the assembly of the detachment system 200.

In a similar manner as with detachment system 100, energy may be stored within the system with, for example, an optional compressive spring 116 or by pre-tensioning the tether 104 during assembly as previously described. When present, the release of potential energy stored in the system operates to apply additional pressure to separate the implant device 112, and the portion of the stretch resistant tether 104 to which the implant device 112 is coupled, away from the heater 206 when the implant device 112 is deployed. This advantageously lowers the required detachment time and temperature by causing the tether 104 to sever and break.

As with detachment system 100, the distal end of the stretch resistant tether 104 of detachment system 200 may be tied or coupled to the distal end of the implant device 112, or may be melted or otherwise formed into an atraumatic distal end 114.

Figure 4:
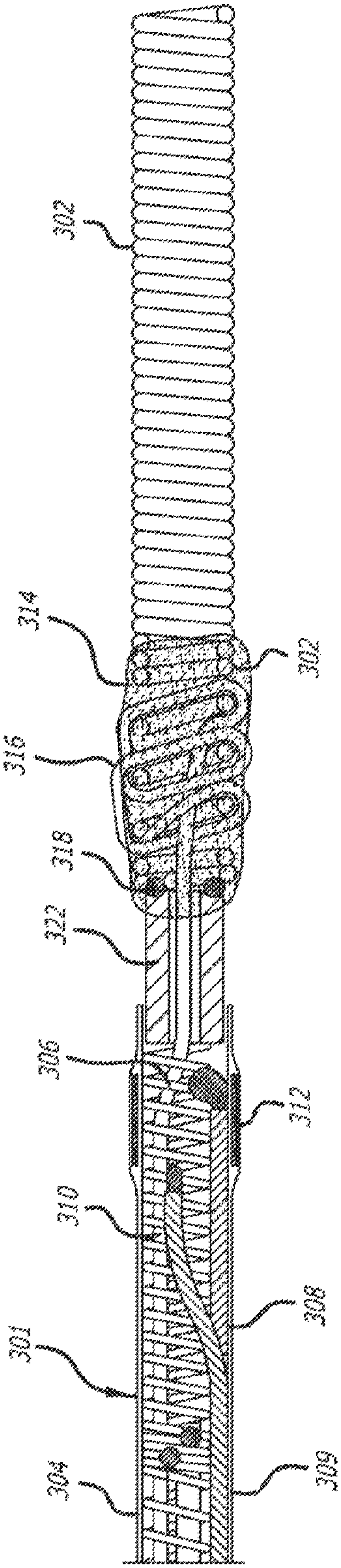
FIG. 4 illustrates a cross-sectional side view of a third embodiment of a detachment system according to the present invention.

FIG. 4 illustrates another preferred embodiment of a detachment system 300. In many respects, the detachment system 300 is similar to the detachment system 200 shown in FIG. 2 and detachment system 100 shown in FIG. 1. For example, the detachment system 300 includes a delivery pusher 301 containing a heater 306 that detaches an implant device 302. Detachment system 300 also utilizes a tether 310 to couple the implant device 302 to the delivery pusher 301.

In the cross-sectional view of FIG. 4, a distal end of the delivery pusher 301 is seen to have a coil-shaped heater 306 that is electrically coupled to electrical wires 308 and 309. These wires 308, 309 are disposed within the delivery pusher 301, exiting at a proximal end of the delivery pusher 301 and coupling to a power supply (not shown). The tether 310 is disposed in proximity to the heater 306, having a proximal end fixed within the delivery pusher 301 and a distal end coupled to the implant device 302. As current is applied through wires 308 and 309, the heater 306 increases in temperature until the tether 310 breaks, releasing the implant device 302.

To reduce the transfer of heat from the heater 306 to the surrounding tissue of the patient and to provide electrical insulation, an insulating cover 304 is included around at least the distal end of the outer surface of the delivery pusher 301. As the thickness of the cover 304 increases, the thermal insulating properties also increase. However, increased thickness also brings increased stiffness and a greater diameter to the delivery pusher 301 that could increase the difficulty of performing a delivery procedure. Thus, the cover 304 is designed with a thickness that provides sufficient thermal insulating properties without overly increasing its stiffness.

To enhance attachment of the tether 310 to the implant device 302, the implant device 302 may include a collar member 322 welded to the implant device 302 at weld 318 and sized to fit within the outer reinforced circumference 312 of the delivery pusher 301. The tether 310 ties around the proximal end of the implant device 302 to form knot 316. Further reinforcement is provided by an adhesive 314 that is disposed around the knot 316 to prevent untying or otherwise unwanted decoupling.

In a similar manner as with detachment systems 100 and 200, energy may be stored within the system with, for example, an optional compressive spring (similar to compressive spring 116 in FIG. 1 but not shown in FIG. 4) or by axially pre-tensioning the tether 104 during assembly. In this embodiment, one end of the tether 310 is attached near the proximal end of the implant device 302 as previously described. The free end of the tether 310 is threaded through a distal portion of the delivery pusher 301 until it reaches an exit point (not shown) of the delivery pusher 301. Tension is applied to the tether 310 in order to store energy in the form of elastic deformation within the tether material by, for example, placing a pre-determined force on the free end of the tether 310 or moving the taut tether 310 a pre-determined displacement. The free end of the tether 310 is then joined to the delivery pusher 301 by, for example, tying a knot, applying adhesive, or similar methods known in the art.

When present, the release of potential energy stored in the system operates to apply additional pressure to separate the implant device 302, and the portion of the tether 310 to which the implant device 302 is coupled, away from the heater 306 when the implant device 302 is deployed. This advantageously lowers the required detachment time and temperature by causing the tether 310 to sever and break.

The present invention also provides for methods of using detachment systems such as detachment systems 100, 200, or 300. The following example relates to the use of detachment system 100, 200, or 300 for occluding cerebral aneurysms. It will, however, be appreciated that modifying the dimensions of the detachment system 100, 200, or 300 and the component parts thereof and/or modifying the implant device 112, 302 configuration will allow the detachment system 100, 200, or 300 to be used to treat a variety of other malformations within a body.

With this particular example, the delivery pusher 102, 202, or 301 of the detachment system 100, 200, or 300 may be approximately 0.010 inches to 0.030 inches in diameter. The tether 104, 310 that is coupled near the distal end of the delivery pusher 102, 202, or 301 and is coupled to the implant device 112, 302 may be 0.0002 inches to 0.020 inches in diameter. The implant device 112, 302; which may be a coil, may be approximately 0.005 inches to 0.020 inches in diameter and may be wound from 0.0005 inch to 0.005 inch wire.

If potential energy is stored within the detachment system 100, 200, or 300, the force used to separate the implant device 112, 302 typically ranges up to 250 grams.

The delivery pusher 102, 202, or 301 may comprise a core mandrel 218 and at least one electrically conductive wire 108, 110, 208, 210, 308, or 309. The core mandrel 218 may be used as an electrical conductor, or a pair of conductive wires may be used, or a bipolar wire may be used as previously described.

Figure 8:
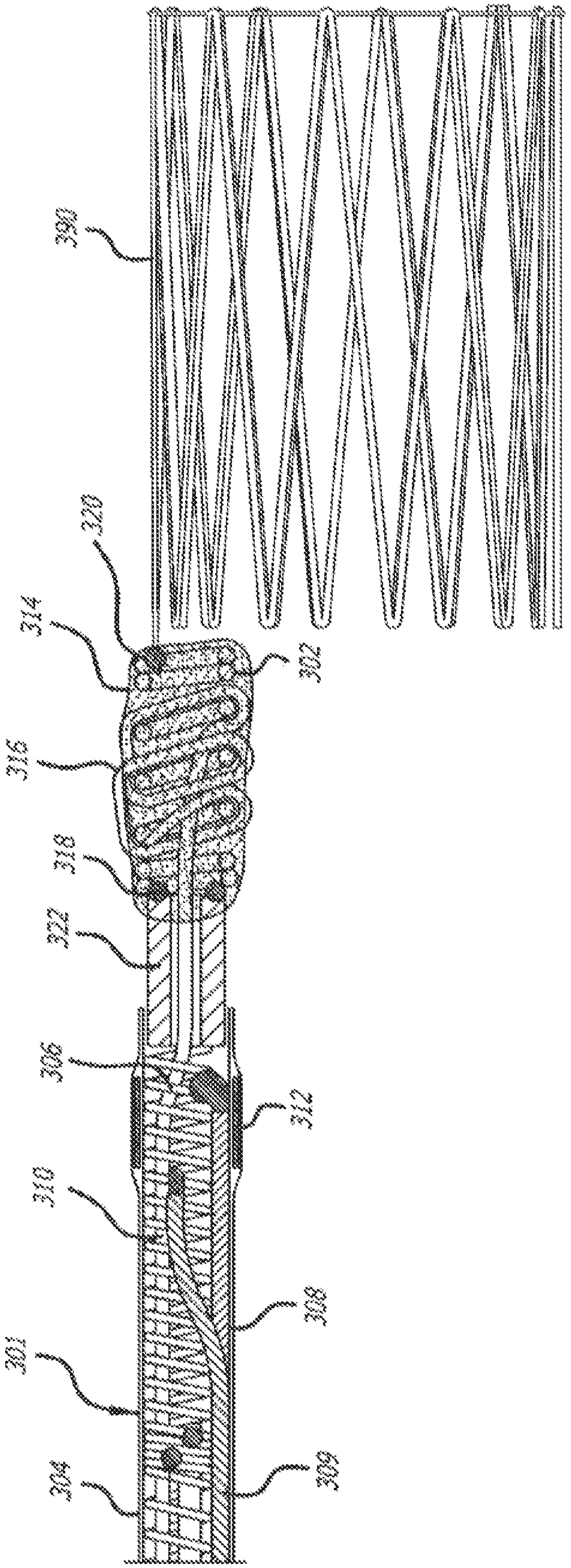
FIG. 8 illustrates a cross-sectional side view of a detachment system including a stent according to the present invention.

Although the detachment systems 100, 200, and 300 have been illustrated as delivering a coil, other implant devices are contemplated in the present invention. For example, FIG. 8 illustrates the detachment system 300 as previously described in FIG. 4 having an implant that is a stent 390. This stent 390 could similarly be detached by a similar method as previously described in regards to the detachment systems 100, 200, and 300. In a further example, the detachment systems 100, 200, or 300 may be used to deliver a filter, mesh, scaffolding or other medical implant suitable for delivery within a patient.

Figure 7:
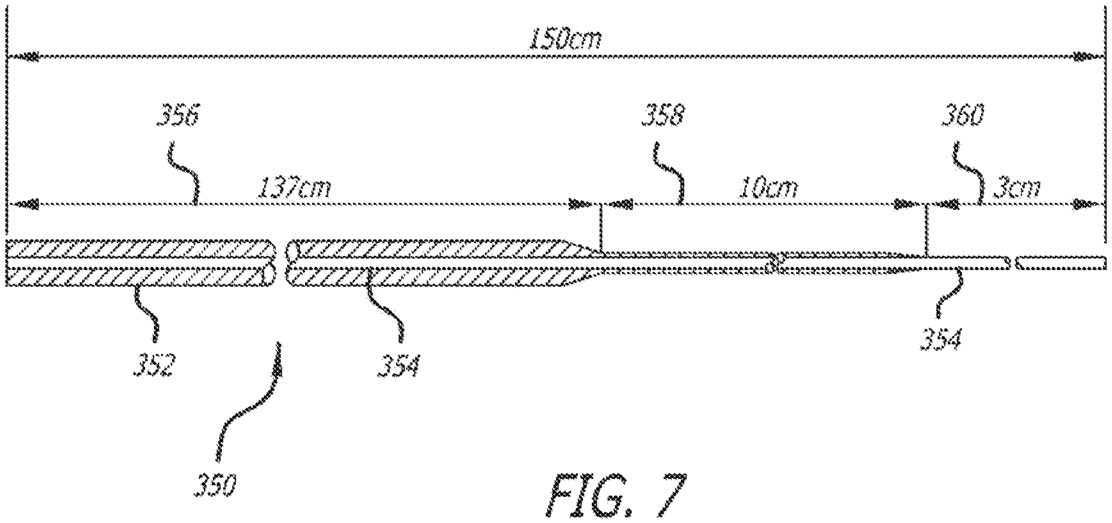
FIG. 7 illustrates a cross-sectional side view of radiopaque layers of a detachment system according to the present invention.

FIG. 7 presents an embodiment of a core wire 350, which could be used in any of the embodiments as delivery pusher 102, 202, or 301, which includes radiopaque materials to communicate the position of the core wire 350 to the user. Specifically, the radiopaque marker material is integrated into the core wire 350 and varied in thickness at a desired location, facilitating easier and more precise manufacturing of the final core wire 350.

Prior delivery pusher designs, such as those seen in U.S. Pat. No. 5,895,385 to Guglielmi, rely on high-density material such as gold, tantalum, tungsten, or platinum in the form of an annular band or coil. The radiopaque marker is then bonded to other, less dense materials, such as stainless steel, to differentiate the radiopaque section. Since the radiopaque marker is a separate element placed at a specified distance (often about 3 cm) from the tip of the delivery pusher, the placement must be exact or the distal tip of the delivery pusher can result in damage to the aneurysm or other complications. For example, the delivery pusher may be overextended from the microcatheter to puncture an aneurysm. Additionally, the manufacturing process to make a prior delivery pusher can be difficult and expensive, especially when bonding dissimilar materials.

The radiopaque system of the present invention overcomes these disadvantages by integrating a first radiopaque material into most of the core wire 350 while varying the thickness of a second radiopaque material, thus eliminating the need to bond multiple sections together. As seen in FIG. 7, the core wire 350 comprises a core mandrel 354 (i.e. the first radiopaque material), preferably made from radiopaque material such as tungsten, tantalum, platinum, or gold (as opposed to the mostly radiolucent materials of the prior art designs such as steel, Nitinol, and Elgiloy).

The core wire 350 also includes a second, outer layer 352, having a different radiopaque level. Preferably, outer layer 352 is composed of a material having a lower radiopaque value than the core mandrel 354, such as Elgiloy, Nitinol, or stainless steel (commercially available from Fort Wayne Metals under the trade name DFT). In this respect, both the core mandrel 354 and the outer layer 352 are visible and distinguishable from each other under fluoroscopy. The outer layer 352 varies in thickness along the length of the core wire 350 to provide increased flexibility and differentiation in radio-density. Thus the thicker regions of the outer layer 352 are more apparent to the user than the thinner regions under fluoroscopy.

The transitions in thickness of the outer layer 352 can be precisely created at desired locations with automated processes such as grinding, drawing, or forging. Such automated processes eliminate the need for hand measuring and placement of markers and further eliminates the need to bond a separate marker element to other radiolucent sections, thus reducing the manufacturing cost and complexity of the system.

In the present embodiment, the core wire 350 includes three main indicator regions of the outer layer 352. A proximal region 356 is the longest of the three at 137 cm, while a middle region 358 is 10 cm and a distal region 360 is 3 cm. The length of each region can be determined based on the use of the core wire 350. For example, the 3 cm distal region 360 may be used during a coil implant procedure, as known in the art, allowing the user to align the proximal edge of the distal region 360 with a radiopaque marker on the microcatheter within which the core wire 350 is positioned. The diameter of each of the regions depends on the application and size of the implant. For a typical cerebral aneurysm application for example, the proximal region 356 may typically measure 0.005-0.015 inches, the middle region 358 may typically measure 0.001-0.008 inches, while the distal region 360 may typically measure 0.0005-0.010 inches. The core mandrel 354 will typically comprise between about 10-80% of the total diameter of the core wire 350 at any point.

Alternately, the core wire 350 may include any number of different regions greater than or less than the three shown in FIG. 7. Additionally, the radiopaque material of the core mandrel 354 may only extend partially through the core wire 350. For example, the radiopaque material could extend from the proximal end of the core mandrel 354 to three centimeters from the distal end of the core wire 350, providing yet another predetermined position marker visible under fluoroscopy.

In this respect, the regions 356, 358, and 360 of core wire 350 provide a more precise radiopaque marking system that is easily manufactured, yet is readily apparent under fluoroscopy. Further, the increased precision of the markers may decrease complications relating to improper positioning of the delivery pusher during a procedure.

In operation, the microcatheter is positioned within a patient so that a distal end of the microcatheter is near a target area or lumen. The core wire 350 (within a delivery device) is inserted into the proximal end of the microcatheter and the core mandrel 354 and outer layer 352 are viewed under fluoroscopy. The user aligns a radiopaque marker on the microcatheter with the beginning of the distal region 360, which communicates the location of the implant 112, 302 relative to the tip of the microcatheter.

In some situations, for example, small aneurysms where there may be an elevated risk of vessel damage from the stiffness of the core wire 350, the user may position the proximal end of the implant slightly within the distal end of the microcatheter during detachment. The user then may push the proximal end of the implant 112, 302 out of the microcatheter with the next coil, an adjunctive device such as guidewire, or the delivery device 102, 202, or 301. In another embodiment, the user may use the radiopaque marking system to locate the distal end of the delivery pusher outside the distal end of the microcatheter.

Once the implant device 112, 302 of the detachment system 100, 200, or 300 is placed in or around the target site, the operator may repeatedly reposition the implant device 112, 302 as necessary or desired.

When detachment of the implant device 112, 302 at the target site is desired, the operator applies energy to the heater 106, 206, or 306 by way of the electrical wires 108, 110, 208, 210, 308, or 309. The electrical power source for the energy may be any suitable source, such as, e.g., a wall outlet, a capacitor, a battery, and the like. For one aspect of this method, electricity with a potential of approximately 1 volt to 100 volts is used to generate a current of 1 milliamp to 5000 milliamps, depending on the resistance of the detachment system 100, 200, or 300.

Figure 6:
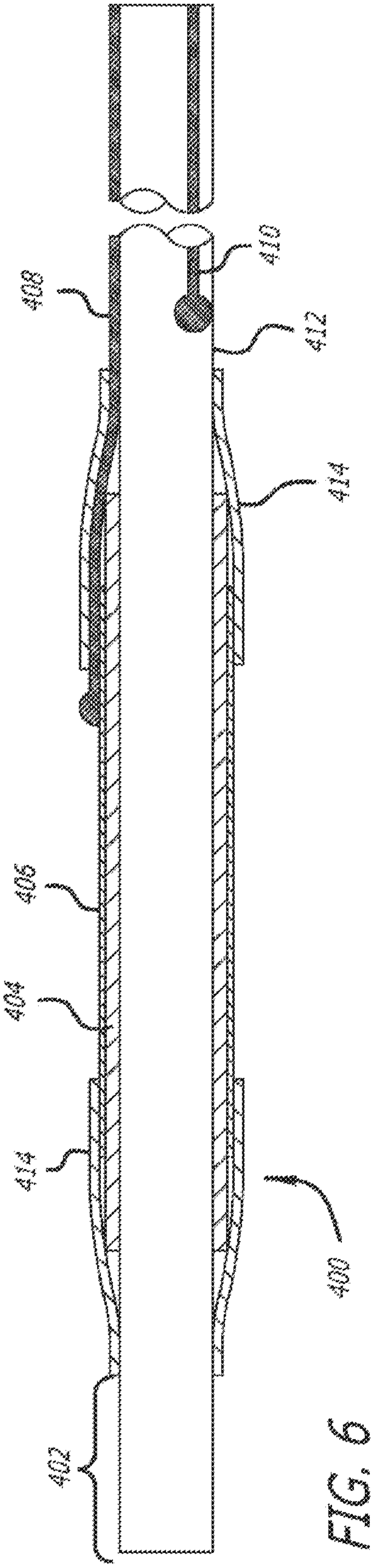
FIG. 6 illustrates a cross-sectional side view of an electrical connector of a detachment system according to the present invention.

One embodiment of a connector system 400 that can be used to electrically couple the detachment system 100, 200, or 300 to the power source is shown in FIG. 6. The connector system 400 includes an electrically conductive core mandrel 412 having a proximal end surrounded by an insulating layer 404. Preferably the insulating layer 404 is an insulating sleeve such as a plastic shrink tube of polyolefin, PET, Nylon, PEEK, Teflon, or polyimide. The insulating layer 404 may also be a coating such as polyurethane, silicone, Teflon, paralyene. An electrically conductive band 406 is disposed on top of the insulating layer 404 and secured in place by molding bands 414, adhesive, or epoxy. Thus, the core mandrel 412 and the conductive band 406 are electrically insulated from each other. The conductive band 406 is preferably composed of any electrically conductive material, such as silver, gold, platinum, steel, copper, conductive polymer, conductive adhesive, or similar materials, and can be a band, coil, or foil. Gold is especially preferred as the conductive material of the conductive band 406 because of the ability of gold to be drawn into a thin wall and its ready availability. The core mandrel 412 has been previously described and may be plated with, for example, gold, silver, copper, or aluminum to enhance its electrical conductivity.

The connector system 400 also includes two electrical wires 408 and 410 which connect to the conductive band 406 and core member 412, respectively, and to a heating element at the distal end of a delivery system such as those described in FIGS. 1, 2, and 4 (not shown in FIG. 6). These wires 408 and 410 are preferably connected by soldering, brazing, welding, laser bonding, or conductive adhesive, or similar techniques.

Once the user is ready to release the implant 112, 302 within the patient, a first electrical clip or connector from a power source is connected to a non-insulated section 402 of the core mandrel 412 and a second electrical clip or connector from the power source is connected to the conductive band 406. Electrical power is applied to the first and second electrical clips, forming an electrical circuit within the detachment system 100, 200, or 300, causing the heater 106, 206, or 306 to increase in temperature and sever the tether 104, 310.

Once the detachment system 100, 200, or 300 is connected to the power source the user may apply a voltage or current as previously described. This causes the heater 106, 206, or 306 to increase in temperature. When heated, the pre-tensioned tether 104, 310 will tend to recover to its unstressed (shorter) length due to heat-induced creep. In this respect, when the tether 104, 310 is heated by the heater 106, 206, or 306; its overall size shrinks. However, since each end of the tether 104, 310 is fixed in place as previously described, the tether 104, 310 is unable to shorten in length, ultimately breaking to release the implant device 112, 302.

Because there is tension already within the system in the form of a spring 116 or deformation of the tether material 104, 310; the amount of shrinkage required to break the tether 104, 310 is less than that of a system without a pre-tensioned tether. Thus, the temperature and time required to free the implant device 112, 302 is lower.

Figure 5:
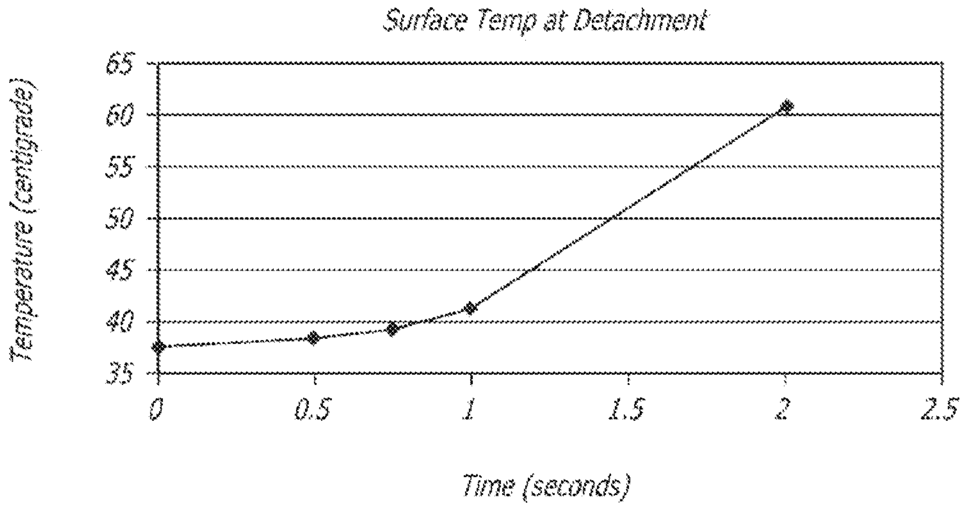
FIG. 5 illustrates example temperature data of the surface of a detachment system according to the present invention.

FIG. 5 is a graph showing the temperatures at the surface of the PET cover 304 of the detachment system 300. As can be seen, the surface temperature of the detachment system 300 during detachment does not vary linearly with time. Specifically, it only takes just under 1 second for the heat generated by the heating coil 306 to penetrate the insulating cover 304. After 1 second, the surface temperature of the insulating cover 304 dramatically increases. Although different outer insulating material may slightly increase or decrease this 1-second surface temperature window, the necessarily small diameter of the detachment system 100, 200, or 300 prevents providing a thick insulating layer that may more significantly delay a surface temperature increase.

It should be understood that the embodiments of the detachment system 100, 200, or 300 include a variety of possible constructions. For example, the insulating cover 304 may be composed of Teflon, PET, polyamide, polyimide, silicone, polyurethane, PEEK, or materials with similar characteristics. In the embodiments 100, 200, or 300 the typical thickness of the insulating cover is 0.0001-0.040 inches. This thickness will tend to increase when the device is adapted for use in, for example, proximal malformations, and decrease when the device is adapted for use in more distal, tortuous locations such as, for example, cerebral aneurysms.

In order to minimize the damage and possible complications caused by such a surface temperature increase, the present invention detaches the implant device 112, 302 before the surface temperature begins to significantly increase. Preferably, the implant device 112, 302 is detached in less than a second, and more preferably, in less than 0.75 seconds. This prevents the surface temperature from exceeding 50° C. (122° F.), and more preferably, from exceeding 42° C. (107° F.).

Once the user attempts to detach the implant device 112, 302, it is often necessary to confirm that the detachment has been successful. The circuitry integrated into the power source may be used to determine whether or not the detachment has been successful. In one embodiment of the present invention an initial signaling current is provided prior to applying a detachment current (i.e. current to activate the heater 106, 206, or 306 to detach an implant 112, 302). The signaling current is used to determine the inductance in the system before the user attempts to detach the implant and therefore has a lower value than the detachment current, so as not to cause premature detachment. After an attempted detachment, a similar signaling current is used to determine a second inductance value that is compared to the initial inductance value. A substantial difference between the initial inductance and the second inductance value indicates that the implant 112, 302 has successfully been detached, while the absence of such a difference indicates unsuccessful detachment. In this respect, the user can easily determine if the implant 112, 302 has been detached, even for delivery systems that utilize nonconductive temperature sensitive polymers to attach an implant, such as those seen in FIGS. 1, 2, and 4.

In the following description and examples, the terms "current" and "electrical current" are used in the most general sense and are understood to encompass alternating current (AC), direct current (DC), and radiofrequency current (RF) unless otherwise noted. The term "changing" is defined as any change in current with a frequency above zero, including both high frequency and low frequency. When a value is measured, calculated and/or saved, it is understood that this may be done either manually or by any known electronic method including, but not limited to, an electronic circuit, semiconductor, EPROM, computer chip, computer memory such as RAM, ROM, or flash; and the like. Finally, wire windings and toroid shapes carry a broad meaning and include a variety of geometries such as circular, elliptical, spherical, quadrilateral, triangular, and trapezoidal shapes.

When a changing current passes through such objects as wire windings or a toroid, it sets up a magnetic field. As the current increases or decreases, the magnetic field strength increase or decreases in the same way. This fluctuation of the magnetic field causes an effect known as inductance, which tends to oppose any further change in current. Inductance (L) in a coil wound around a core is dependant on the number of turns (N), the cross-sectional area of the core (A), the magnetic permeability of the core (u), and length of the coil (l) according to equation 1 below:

$$L = \frac{.4\pi N^2 A\mu}{l} \qquad \text{Equation 1}$$

Figure 3A:
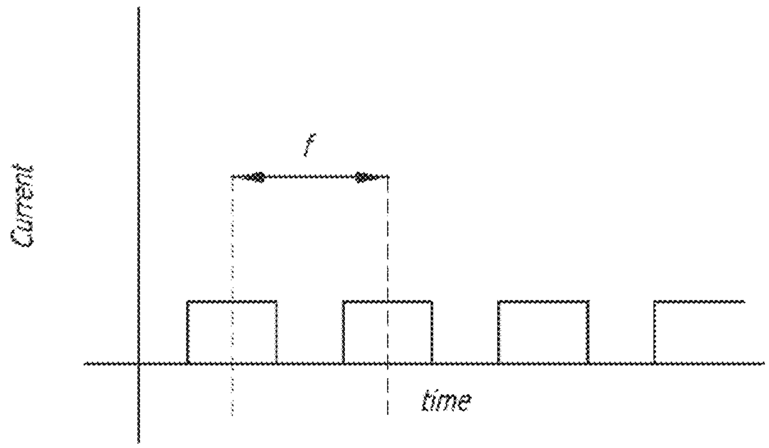
FIG. 3A illustrates example direct signaling current according to the present invention.
Figure 3B:
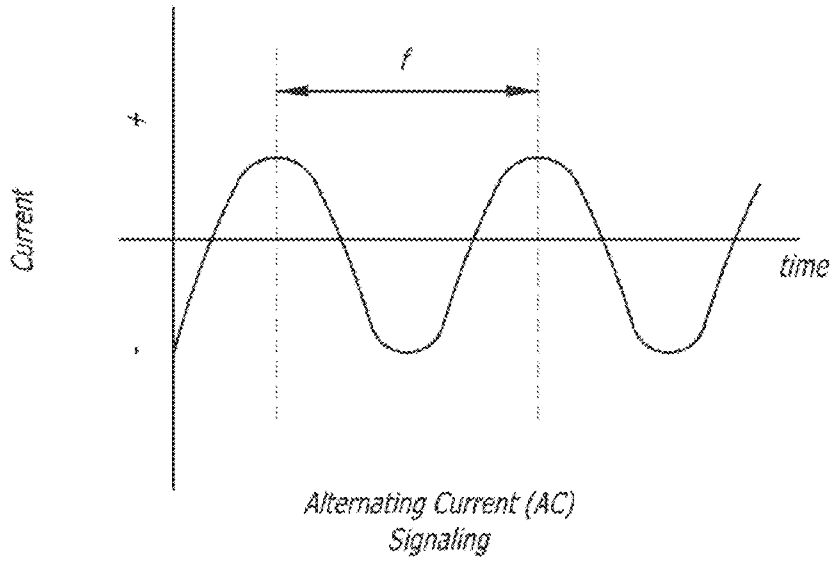
FIG. 3B illustrates example alternating signaling current according to the present invention.

The heater 106 or 306 is formed from a wound coil with proximal and distal electrically conductive wires 108, 110, 308, or 309 attached to a power source. The tether 104, 310 has a magnetic permeability μ1 and is positioned through the center of the resistive heater, having a length l, cross sectional area A, and N winds, forming a core as described in the previous equation. Prior to detachment, a changing signaling current i1, such as the waveforms shown in FIGS. 3A and 3B, with frequency f1, is sent through the coil windings. This signaling current is generally insufficient to detach the implant. Based on the signaling current, the inductive resistance XL (i.e. the electrical resistance due to the inductance within the system) is measured by an electronic circuit such as an ohmmeter. The initial inductance of the system L1 is then calculated according to the formula:

$$L_1 = \frac{X_L}{2\pi f_1} \qquad \text{Equation 2}$$

This initial value of the inductance L1 depends on the magnetic permeability μ1 of the core of the tether 104, 310 according to Equation 1, and is saved for reference. When detachment is desired, a higher current and/or a current with a different frequency than the signaling current is applied through the resistive heater coil, causing the tether 104, 310 to release the implant 112, 302 as previously described. If detachment is successful, the tether 104, 310 will no longer be present within the heater 106, 306 and the inside of the heater 106, 306 will fill with another material such as the patient's blood, contrast media, saline solution, or air. This material now within the heater core will have a magnetic permeability μ2 that is different than the tether core magnetic permeability μ1.

A second signaling current and frequency f2 is sent through the heater 106, 306 and is preferably the same as the first signaling current and frequency, although one or both may be different without affecting the operation of the system. Based on the second signaling current, a second inductance L2 is calculated. If the detachment was successful, the second inductance L2 will be different (higher or lower) than the first inductance L1 due to the difference in the core magnetic permeabilities μ1 and μ2. If the detachment was unsuccessful, the inductance values should remain relatively similar (with some tolerance for measurement error). Once detachment has been confirmed by comparing the difference between the two inductances, an alarm or signal can be activated to communicate successful detachment to the user. For example, the alarm might include a beep or an indicator light.

Preferably, the delivery system 100, 300 used according to this invention connects to a device that automatically measures inductance at desired times, performs required calculations, and signals to the user when the implant device has detached from the delivery catheter. However, it should be understood that part or all of these steps can be manually performed to achieve the same result.

The inductance between the attached and detached states can also preferably be determined without directly calculating the inductance. For example, the inductive resistance XL can be measured and compared before and after detachment. In another example, the detachment can be determined by measuring and comparing the time constant of the system, which is the time required for the current to reach a predetermined percentage of its nominal value. Since the time constant depends on the inductance, a change in the time constant would similarly indicate a change in inductance.

The present invention may also include a feedback algorithm that is used in conjunction with the detachment detection described above. For example, the algorithm automatically increases the detachment voltage or current automatically after the prior attempt fails to detach the implant device. This cycle of measurement, attempted detachment, measurement, and increased detachment voltage/current continues until detachment is detected or a predetermined current or voltage limit is attained. In this respect, a low power detachment could be first attempted, followed automatically by increased power or time until detachment has occurred. Thus, battery life for a mechanism providing the detachment power is increased while the average coil detachment time is greatly reduced.

Figure 9:
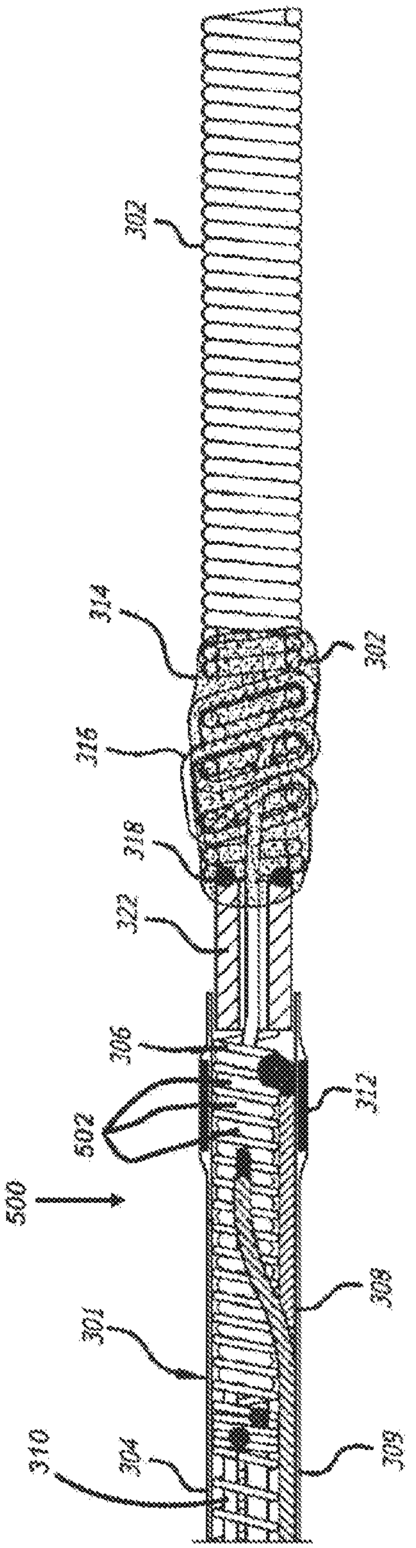
FIG. 9 illustrates a side view of a implant device according to the present invention.
Figure 10:
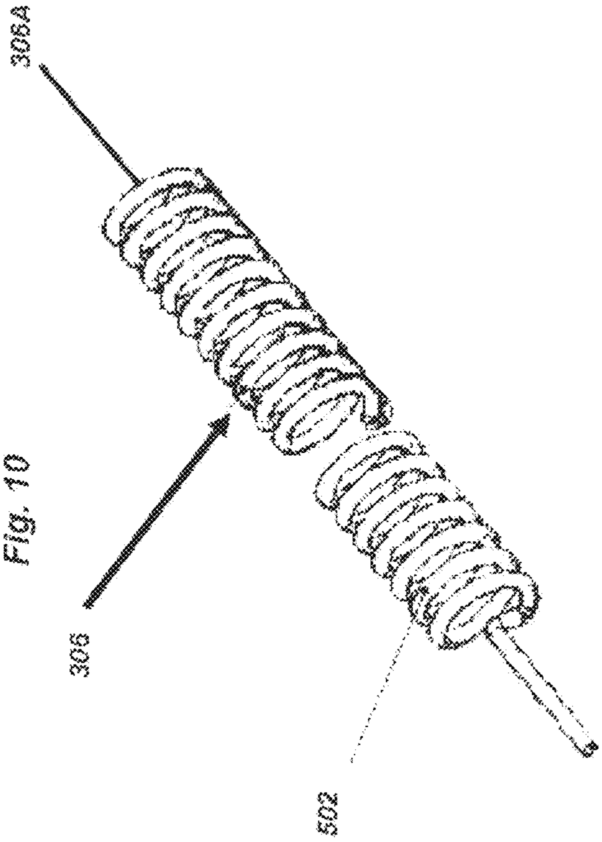
FIG. 10 illustrates a perspective view of a coil and spacer of the delivery system of FIG. 9.

Referring now to FIGS. 9 and 10, there is shown an embodiment of a delivery system 500 for use with the present invention that includes a detachment detection capability. The delivery system 500 operates under the principle that electrical current passing through a coil held in an expanded, open gap configuration will encounter more resistance than electrical current passing through a coil in a contracted, closed gap configuration. In the expanded configuration, the electrical current must follow the entire length of the coiled wire. In the contracted configuration, the electrical current can bridge the coils and travel in a longitudinal direction.

The delivery system 500 is generally similar to the previously described detachment system 300 of the present invention seen in FIG. 4, including a delivery pusher 301, containing a heater coil 306 that detaches an implant device 302. The detachment system 500 similarly utilizes a tether 310 to coupled the implant device 302 to the delivery pusher 301.

The heater coil 306 is preferably a resistance-type heater having a plurality of loops 306A as seen in FIG. 10, that connects to a voltage source through a connector system at the proximal end of the delivery pusher 301, such as the connector system 400 described in FIG. 6.

The delivery system 500 also includes a heater coil expander 502 that serves two functions. First, it expands the heater coil 306 such that the heater coil 306 maintains a friction-fit attachment to the inside of the insulating cover 309, thereby connecting the two. Second, the heater coil expander 502 expands the heater coil 306 in such a manner that electricity is forced to flow around each individual loop 306A of the coil 306 in order to maximize the resistance of the coil 306.

Maximizing the coil resistance not only serves to heat the coil 306 when voltage is passed through, it also sets an initial value (or "normal" value) for the resistance provided by the coil 306, which can be used to compare a changed resistance state, indicating detachment of the implant 302. Hence, the heater coil expander 502 must also be capable of undergoing change when subjected to heat. In this regard, the heater coil expander 502 may be made of any suitable sturdy material capable of holding the heater coil 306 in an expanded, biased state while also being capable of melting or being otherwise reduced by the heat of the heater coil 306 in order to yield to the bias of the heater coil 306 to return to an unbiased state. Examples of acceptable materials include, but are not limited to, polymers and monofilament.

The heater coil expander 502 shown in FIGS. 9 and 10 operates by longitudinally, or radially and longitudinally, expanding a heater coil 306 which is normally a closed gap coil in a relaxed state. In other words, the individual loops 306A contact each other when the heater coil 306 is not stretched or radially expanded. Preferably, the heater coil expander 502 may have a coiled shape, similar to the heater coil 306 and as seen in FIG. 10. Alternately, the heater coil expander may have a continuous, tubular shape with helical ridges similar to the individual coil shapes of the expander 502 in FIG. 10. It should be understood that a variety of different expander shapes that expand the loops or coils 306A of the heater coil 306 from each other.

Preferably the power source (previously described in this embodiment and connected to the connector system 400) also includes a measuring instrument for measuring the resistance of the heater coil 306. In this respect, the power source (preferably located in a hand-sized unit) includes an indicator that communicates when a change in resistance has occurred and therefore when detachment of the implant has occurred.

Figure 11:
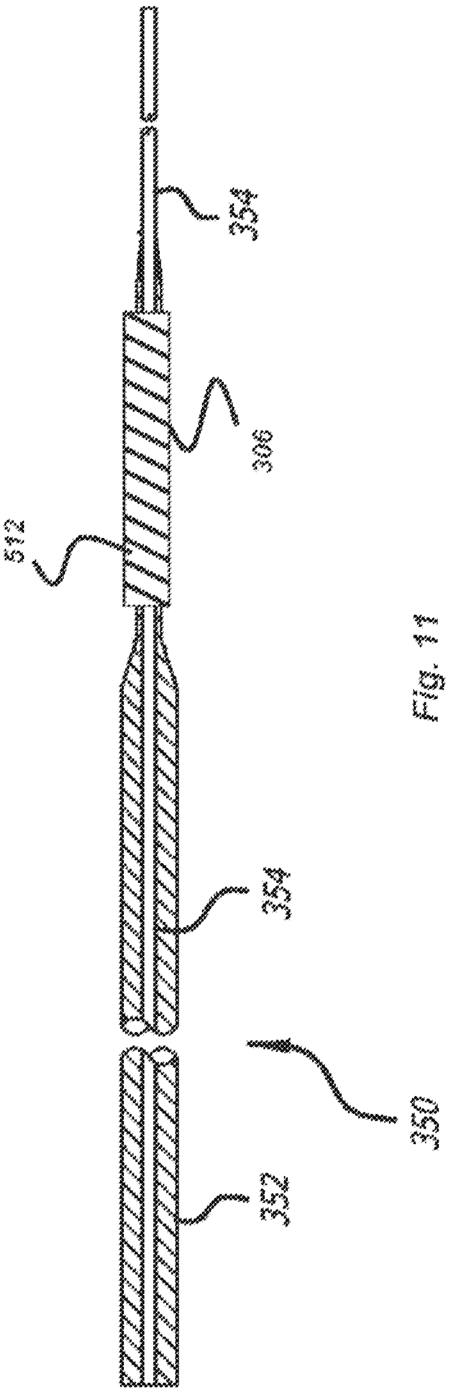
FIG. 11 illustrates a side view of a pusher of the delivery system of according to the present invention.
Figure 12:
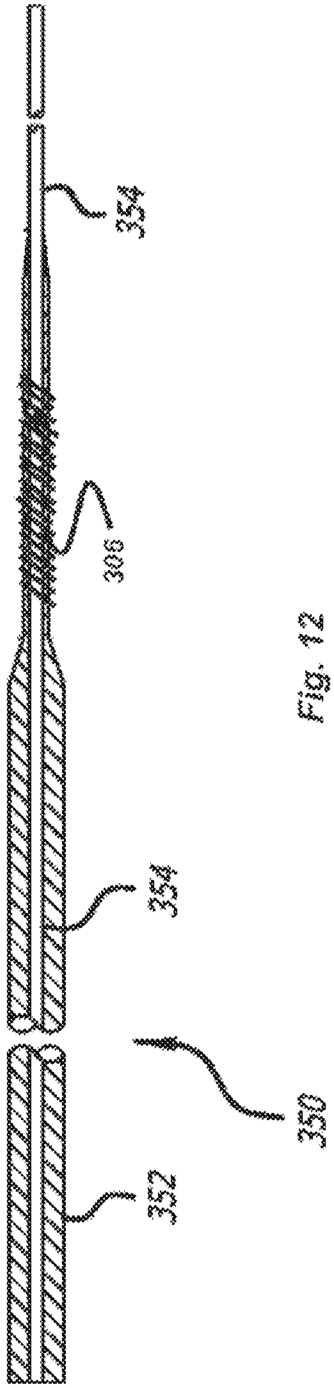
FIG. 12 illustrates a side view of the pusher of the delivery system of FIG. 11.

An alternative embodiment of the heater coil expander 512 is shown in FIGS. 10 and 11. The heater coil expander 512 operates in conjunction with the heater coil 306 so that the heater loops are in an open gap state (FIG. 10), and a core wire 350, as previously described in FIG. 7, that conducts electricity. The heater coil 306 is sized to snugly fit around the core wire 350 in a contracted state. The heater coil expander 512 operates to separate the heater coil 306 from the core wire 350, electrically isolating the heater coil 306 therefrom. As the heat from the heater coil 306 melts or otherwise reduces or degrades the heater coil expander 512, the heater coil 306 resumes a contracted state (i.e., reduced diameter configuration), making electrical, if not physical, contact with the core wire 350 (FIG. 11). In this respect the individual loops are shortened, significantly reducing the resistance of the circuit and thereby indicating detachment has occurred.

Another alternative embodiment of the present invention, the heater coil expander 502 may be sized to expand the heater coil 306 against the conductive reinforcement circumference 312 (shown in FIG. 9). Hence, when the coil 306 is in its initial expanded position, the electrically conductive reinforcement circumference 312 maintains a low initial resistance that is registered by the controller for the circuit (i.e., the measurement device of the power source).

When the heater coil 306 is energized, the initial resistance is noted and the heater coil expander 306 melts, degrades or otherwise reduces. The heater coil 306 then contracts, releasing the attachment tube 512 (and the rest of the implant 510) and the heater coil 522*a* is no longer shorted out by the reinforcement circumference 312. Thus, the circuit experiences a change in resistance as the electrical current must travel through each of the individual loops 524*a*. This increase in resistance signifies the implant 302 is detached.

Figure 13:
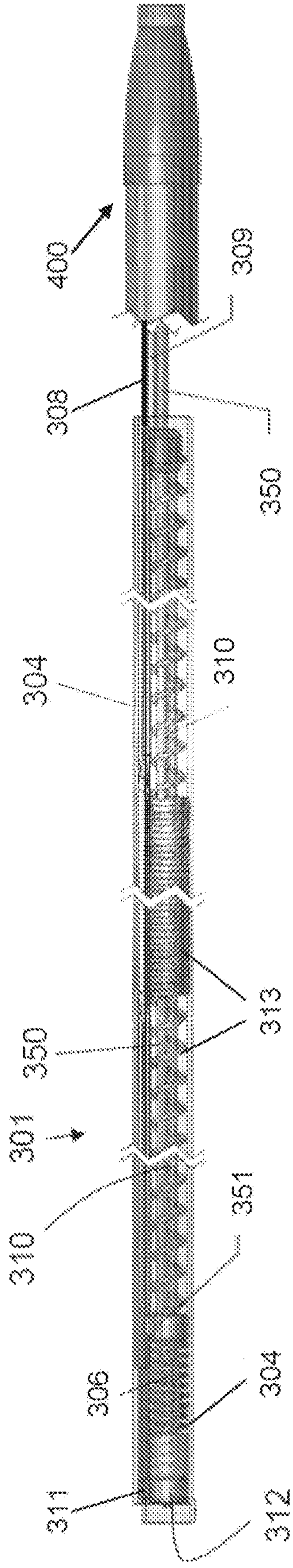
FIG. 13 illustrates a side view of a delivery device according to the present invention.
Figure 14:
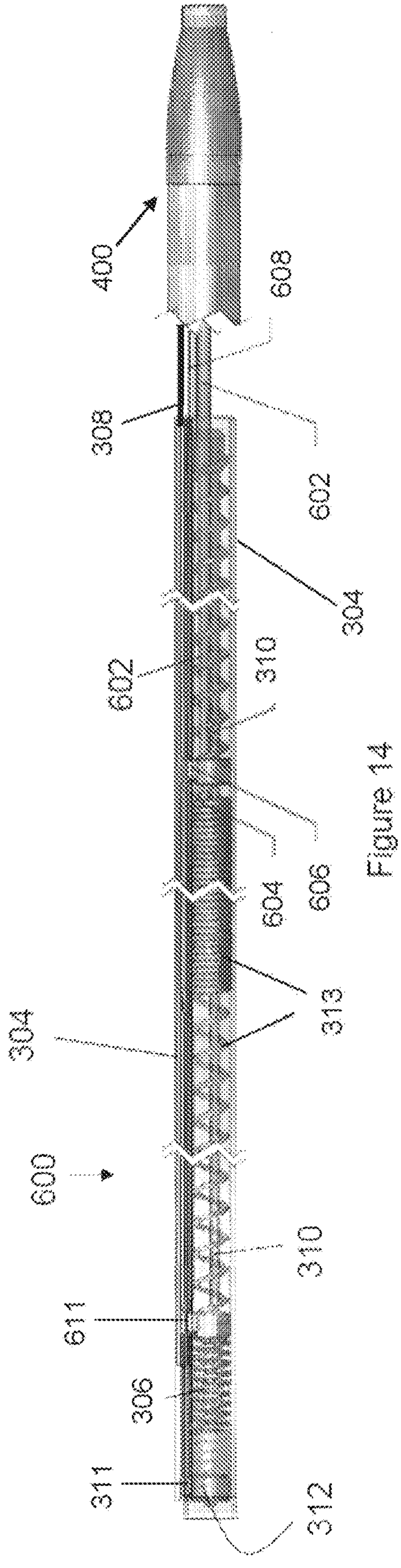
FIG. 14 illustrates a side view of a delivery device according to the present invention.
Figure 15:
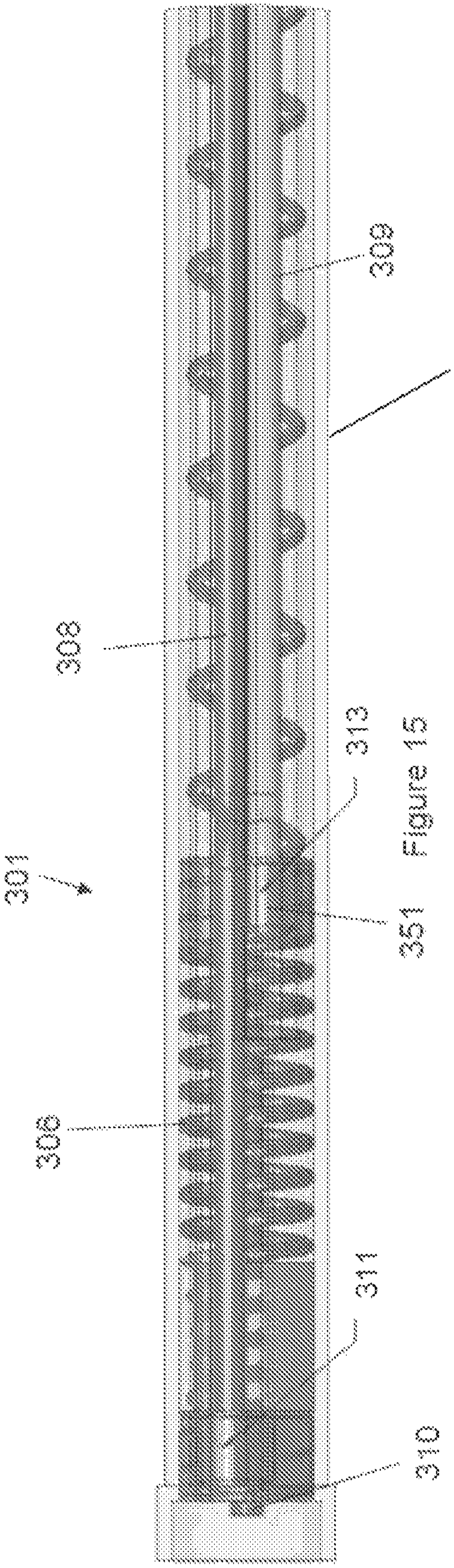
FIG. 15 illustrates a magnified side view of the delivery device of FIG. 13.
Figure 16:
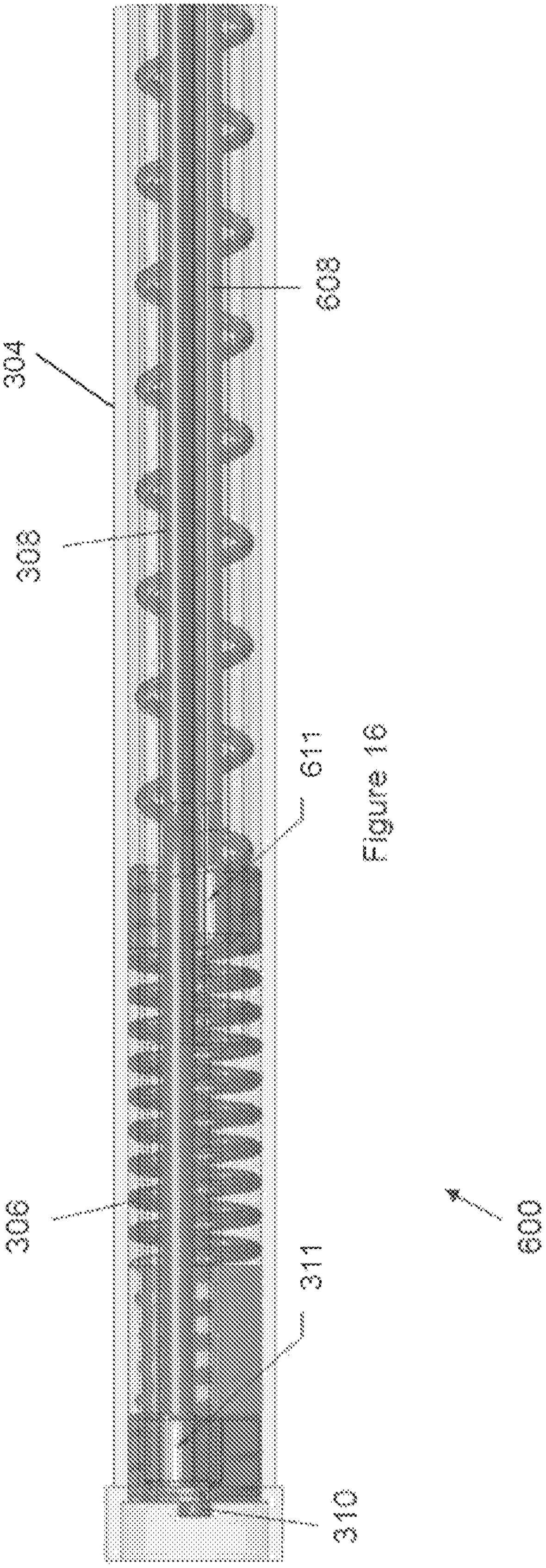
FIG. 16 illustrates a magnified side view of the delivery device of FIG. 14; and, FIG. 17 illustrates a magnified side view of the delivery device of FIG. 14.
Figure 17:
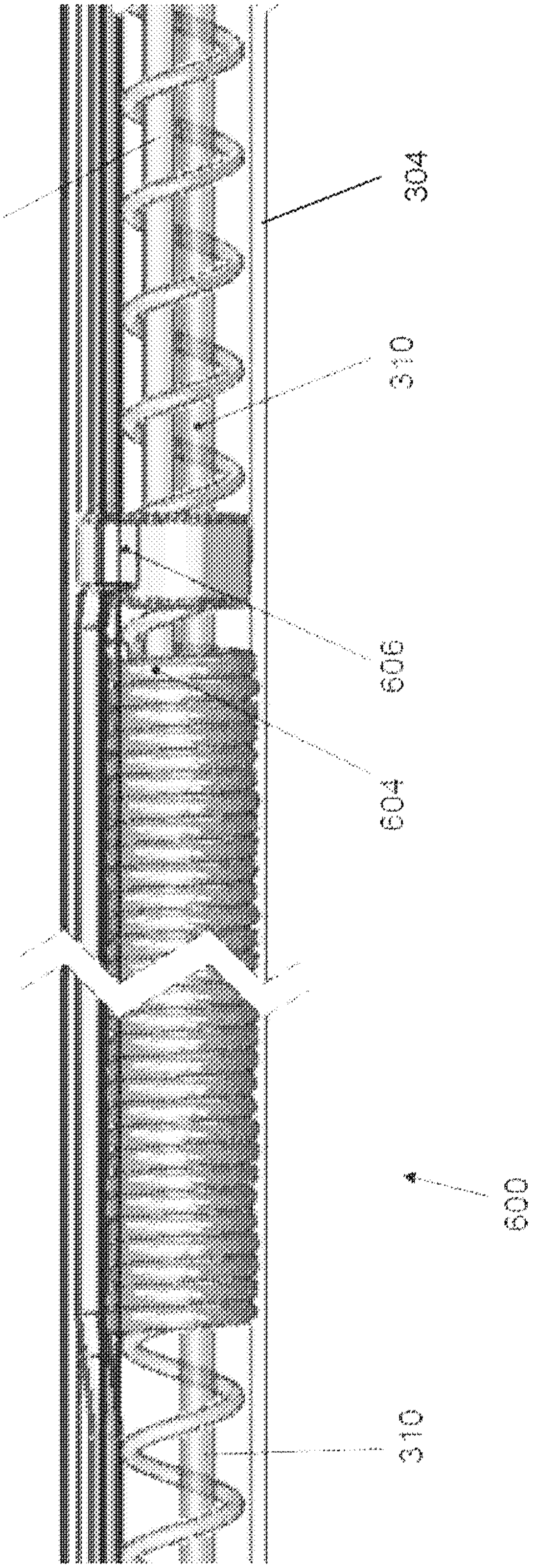

FIGS. 14, 16 and 17 illustrate another preferred embodiment of a delivery pusher 600 according to the present invention which includes a more flexible distal tip than some of the previously described embodiments. FIGS. 13 and 15 illustrate views of the previously described delivery pusher 301 which are provided alongside the figures of the delivery pusher 600 for comparative purposes.

The core wire 350 of the delivery pusher 301, as seen in FIGS. 13 and 15, terminates near the proximal end of the heater coil 306 at the distal end of the delivery pusher 301. In this respect, the distal end of the delivery pusher 301 maintains a moderate amount of rigidity for advancing within a vascular system while allowing enough flexibility to advance through tortuous paths and into a treatment location (e.g., an aneurysm).

While this combination of flexibility and rigidity can be desirable in some treatment locations, other treatment locations would benefit from greater flexibility in the distal end of the treatment device 301. For example, in some locations, a microcatheter may be positioned within an aneurysm but when the implant 302 and delivery device 301 are advanced within the microcatheter (i.e., to push out the implant 302), the delivery device 302 can, in some situations, “kick out” or push the microcatheter out of the aneurysm. In another example, the transition in stiffness between the portion of the delivery device including the core wire 350 and the distal region lacking the core wire 350 can, in some situations, provide a tactile feeling to the physician which could be mistaken for the microcatheter being kicked out of the aneurysm.

The delivery device 600 is generally softer and more flexible than the delivery device 301 at the distal end (e.g., within 3 cm of the distal end) by terminating the core wire 602 at a location more proximal than that of the delivery device 301. For example, the core wire 602 terminates near the 3 cm radiopaque marker (location 604 in FIG. 14), which is 3 cm from the distal end of the device 600 (e.g., the distal portion of sleeve 304). In contrast, the core wire 350 terminates at a location 351 near the proximal end of the heater coil 306 (FIG. 13). The core wire 602 may also preferably terminate between about 2 cm and 4 cm from the distal end of the device 600 (e.g., the distal end of the sleeve 304).

A support coil 313 is located around at least some elements of the device 600, such as the tether 310 and connects to the heater coil 306. The support coil 313 can include different coil densities or frequencies, such as a densely coiled center region and two less-dense end regions as seen in FIG. 14. Since the core wire 602 is a primary contributing factor for the rigidity of the delivery device 600, the distal end of the delivery device 600 is more flexible, being primarily supported by the support coil 313.

This increased flexibility allows less “kick back” or opposing movement of the microcatheter as the delivery device 600 is advance distally within it, and therefore reduces the likelihood of the microcatheter being pushed out of the an aneurysm or lesion.

Additionally, longer or greater number of implants (e.g., such as microcoils) can be used within an aneurysm or lesion. More specifically, as an aneurysm is filled with occluding microcoils, the areas within the aneurysm that can support the position of the microcatheter decrease. Hence, as an aneurysm is filled, it can be difficult to prevent the distal end of the microcatheter from being pushed out by the advancing forces of the delivery device. However, the softer distal tip of the delivery device 600 provides less “kick back” force on the microcatheter and therefore allows the aneurysm to be filled to a greater capacity.

The delivery device 600 further includes an insulated electrical wire 308 terminating at a location 311 near a distal end of the heater coil 306 and to an electrically conductive band on a proximal end of the delivery device 600 (similar to the arrangement shown in FIG. 6). In this regard, the insulation on the wire 308 prevents electrical communication with the core wire 602.

A bare or non-insulated wire 608 terminates at a location 611 near the proximal end of the heater coil 306. The wire 608 is soldered to the core wire 602 in a first location near the proximal end of the core wire 602 (similar to the arrangement shown in FIG. 6) and to a second location 606 near the termination point of the core wire 604.

Preferably, the wire 608 is composed of a material that conducts electricity with little resistance, such as 99.99% silver, and has a diameter of about 0.002 inches. By providing an additional solder point 606 to the core wire 602, additional current carried by the core wire 602 is reduced to zero. In comparison, core wire 350 of the delivery device 301 can, in some situations, carry as much as 40 mA. Hence, the electricity is more efficiently conveyed to the heater coil 306 in the delivery device 600 and can thereby provide more focalized heat around the heater coil 306, allowing for improved detachment performance.

Additionally, by using a bare, non-insulated wire 608 the manufacturing process for the delivery device 600 can be made more reliable. For example, the wire 608 does not require stripping of an insulating coating (e.g., a polyimide coating) at multiple locations. This stripping can result in damage or necking to the wire, which can increase manufacturing costs.

In operation, the connector system 400 is connected to a power supply to selectively supply power to release an implant. When supplied, electricity passes to the proximal end of the core wire 602, on to the proximal end of the non-insulated wire 608, past solder point 606, to the distal end of the of the heater coil 306 at point 611, through the heater coil 306 and into the distal end of the insulated wire 308 at point 311, through the length of the wire 308 and ending at the electrically conductive band in the connector system 400. Alternately, the electricity could take the reverse path.

Although the invention has been described in terms of particular embodiments and applications, one of ordinary skill in the art, in light of this teaching, can generate additional embodiments and modifications without departing from the spirit of or exceeding the scope of the claimed invention. For example, the heater coil or heater coil expander could be constructed to activate a switch that provides a user indication of detachment in some manner. Additionally, a visual indicator may be associated with the change in resistance to provide easy indication of detachment. Accordingly, it is to be understood that the drawings and descriptions herein are proffered by way of example to facilitate comprehension of the invention and should not be construed to limit the scope thereof.

What is claimed is:

1. A delivery device comprising:

an implant releasably located at a distal end of the delivery device;

a heater configured to detach the implant when being activated;

a support coil configured to provide structural support to the delivery device, wherein the support coil is located at a proximal end of the heater, and wherein the support coil comprises a center region at a middle portion of the support coil, a distal region at a distal end of the support coil, and a proximal region at a proximal end of the support coil, wherein a coil density of the center region is higher than a coil density of the distal region and the proximal region;

a core wire connected to the support coil; and a bare wire connected to and in electrical communication with the core wire at both a first location and a second location.

2. The delivery device of claim 1, wherein the bare wire is further connected to and in electrical communication with the heater.

3. The delivery device of claim 2, further comprising an insulated wire in electrical communication with the heater at the distal end of the delivery device.

4. The delivery device of claim 3, wherein the insulated wire is in electrical communication with a conductive band located near a proximal end of the delivery device.

5. The delivery device of claim 4, further comprising:

a power supply connected to the core wire, wherein the power supply supplies electricity that passes first through the core wire, second through the bare wire, third through the heater, and fourth through an insulated wire back to the power supply.

6. The delivery device of claim 1, wherein the core wire comprises at least one radiopaque material.

7. The delivery device of claim 6, wherein the core wire comprises:

a core mandrel comprising:

a proximal portion;

a middle portion; and a distal portion, wherein the core mandrel is composed of a first radiopaque material; and an outer layer covering the proximal portion of the core mandrel and the middle portion of the core mandrel, wherein the outer layer is composed of a second radiopaque material, wherein the second radiopaque material has a lower radiopaque value than the first radiopaque material.

8. The delivery device of claim 7, wherein a thickness of the outer layer varies along a length of the core mandrel.

9. The delivery device of claim 7, wherein the outer layer has a first thickness over the proximal portion of the core mandrel and has a second thickness over the middle portion of the core mandrel, and wherein the first thickness is higher than the second thickness.

10. A delivery device comprising:

an implant releasably located at a distal end of the delivery device;

a heater coil configured to detach the implant when being activated;

a core wire comprising at least two radiopaque materials of different radiopaque values;

a support coil located between a proximal end of the heater coil and a distal end of the core wire, wherein the support coil comprises a first coil region and at least one second coil region, wherein a coil density of the first coil region is higher than a coil density of the at least one second coil region; and a bare wire connected to and in electrical communication with the core wire at both a first location and a second location.

11. The delivery device of claim 10, wherein the core wire comprises:

a core mandrel comprising:

a proximal portion;

a middle portion; and a distal portion, wherein the core mandrel is composed of a first radiopaque material; and an outer layer covering the proximal portion of the core mandrel and the middle portion of the core mandrel, wherein the outer layer is composed of a second radiopaque material, wherein the second radiopaque material has a lower radiopaque value than the first radiopaque material.

12. The delivery device of claim 10, wherein the bare wire is further connected to and in electrical communication with the heater coil.

13. The delivery device of claim 12, further comprising an insulated wire in electrical communication with the heater coil at the distal end of the delivery device.

14. The delivery device of claim 13, wherein the insulated wire is in electrical communication with a conductive band located near a proximal end of the delivery device.

15. The delivery device of claim 14, further comprising:

a power supply connected to the core wire, wherein the power supply supplies electricity that passes first through the core wire, second through the bare wire, third through the heater coil, and fourth through an insulated wire back to the power supply.

16. The delivery device of claim 10, wherein the support coil comprises two second coil regions, wherein the first coil region is positioned between the two second coil regions.

17. A delivery device comprising:

an implant releasably located at a distal end of the delivery device;

a heater configured to detach the implant when being activated;

a support means configured to provide structural support to the delivery device, wherein the support means is located at a proximal end of the heater, and wherein the support means comprises a center region at a middle portion of the support means, a distal region at a distal end of the support means, and a proximal region at a proximal end of the support means, wherein a coil density of the center region is higher than a coil density of the distal region and the proximal region;

a core wire connected to the support means; and a bare wire connected to and in electrical communication with the core wire at both a first location and a second location.

18. The delivery device of claim 11, wherein a thickness of the outer layer varies along a length of the core mandrel.

19. The delivery device of claim 11, wherein the outer layer has a first thickness over the proximal portion of the core mandrel and has a second thickness over the middle portion of the core mandrel, and wherein the first thickness is higher than the second thickness.

* * * * *